US012163185B2

(12) United States Patent
Morley

(10) Patent No.: US 12,163,185 B2
(45) Date of Patent: Dec. 10, 2024

(54) METHOD OF ASSESSMENT

(71) Applicant: Monoquant Pty Ltd., Adelaide (AU)

(72) Inventor: Alexander Alan Morley, Toorak (AU)

(73) Assignee: Monoquant Pty Ltd., Adelaide (AU)

( * ) Notice: Subject to any disclaimer, the term of this patent is extended or adjusted under 35 U.S.C. 154(b) by 755 days.

(21) Appl. No.: 16/999,594

(22) Filed: Aug. 21, 2020

(65) Prior Publication Data

US 2022/0056513 A1 Feb. 24, 2022

(51) Int. Cl.
*C12Q 1/68* (2018.01)
*C12Q 1/6851* (2018.01)

(52) U.S. Cl.
CPC ................... *C12Q 1/6851* (2013.01)

(58) Field of Classification Search
CPC .... C12Q 1/6851; C12Q 1/6811; C12Q 1/686; C12Q 2527/146; C12Q 2531/113; C12Q 2545/114
See application file for complete search history.

(56) References Cited

U.S. PATENT DOCUMENTS

2006/0183144 A1* 8/2006 Willey ................... G16B 50/00
435/6.12

FOREIGN PATENT DOCUMENTS

WO    WO 2015/114009 A1    8/2015

OTHER PUBLICATIONS

Meijerink et al. (J of Molec Diagnostics, 2001, 3(2):55-61) (Year: 2001).*
Rosati et al. (BMC Biotechnology, 2017, 17:61, p. 1-16) (Year: 2017).*
Boyanton et al. (D. Crisan (ed.), Hematopathology, Molecular and Translational Medicine, Chapter 1, p. 1-38, DOI 10.1007/978-1-60761-262-9_1, C _ Springer Science+Business Media, LLC 2010). (Year: 2010).*
Rutledge et al. (PLoS One, 2010, 5(3):e9731:p. 1-11) (Year: 2010).*
Ramakers et al. (Neuroscience Letters, 2003, vol. 339, p. 62-66) (Year: 2003).*
Neale et al. (Leukemia, 2004, 18, 934-938) (Year: 2004).*
Boyanton Jr., Bobby L. "Molecular Techniques in Hematopathology" Hematopathology, Sep. 2010, Chapter 1.
Khorosheva, Eugenia M. et al., "Lack of correlation between reaction speed and analytical sensitivity in isothermal amplification reveals the value of digital methods for optimization: validation using digital real-time RT-LAMP" Nucleic Acids Research, 2016, pp. 1-12, vol. 44, No. 2, e10.
Latham, Susan et al., "Patient-Specific Minimal Residual Disease Primers Amplify with Uniformly High Efficiency" The Journal of Molecular Diagnostics, Mar. 2021, pp. 341-346, vol. 23, No. 3.
Meijerink, Jules et al., "A Novel Method to Compensate for Different Amplification Efficiencies between Patent DNA Samples in Quantitative Real-Time PCR" Journal of Molecular Diagnostics, May 2001, pp. 55-61, vol. 3, No. 2.
Morley, Alexander A. et al., "Patient-Specific MRD Primers Amplify with Uniformly High Efficiency" Blood, 2020, Supplement 1, vol. 136, No. 12.
Neale, Gam et al., "Comparative analysis of flow cytometry and polymerase chain reaction for the detection of minimal residual disease in childhood acute lymphoblastic leukemia" Leukemia, 2004, pp. 934-938, vol. 18.
Ramakers, Christian et al., "Assumption-free analysis of quantitative real-time polymerase chain reaction (PCT) data" Neuroscience Letters, 2003, pp. 62-66, vol. 339.
Rosati, Elisa et al., "Overview of methodologies for T-cell receptor repertoire analysis" BMC Biotechnology, 2017, pp. 1-16, vol. 17, No. 61.
Rutledge, Robert G et al., "Assessing the Performance Capabilities of LRE-Based Assays for Absolute Quantitative Real-Time PCR" PLoS One, Mar. 2010, pp. 1-11, vol. 5, Issue 3, e9731.
Santalucia, Jr., John "A Novel, Validated Method for Absolute QPCR Quantification" 2016, pp. 1-13, DNA Software.
Wang, Zhuo et al., "Comparison of droplet digital PCR and direct Sanger sequencing for the detection of the $BRAF^{V600E}$ mutation in papillary thyroid carcinoma" J Clin Lab Anal., 2019, pp. 1-6, vol. 33, e22902.

* cited by examiner

*Primary Examiner* — Stephanie K Mummert
(74) *Attorney, Agent, or Firm* — Knobbe, Martens, Olson & Bear, LLP

(57) ABSTRACT

Aspects of the present invention relate to methods of assessing the amplification efficiency of a primer especially the relative or absolute efficiency of a primer used in quantitative PCR amplification. Some of the methods described herein involve the assessment of primer efficiency relative to the Ct determined for a single target DNA molecule rather than Ct regression curve analysis of serially diluted samples. By assessing primer efficiency utilizing the approaches described herein, one can more efficiently select primers for the diagnosis and/or monitoring of disease conditions, analysis of specific gene regions of interest, the monitoring of disease conditions that are characterised by clonal lymphoid cell populations or disease conditions that are characterised by specific V(D)J recombination events including the detection of minimal or residual disease in leukaemia patients.

26 Claims, 2 Drawing Sheets

Specification includes a Sequence Listing.

FIGURE 1

Shaded are EcoRI sites
Inserted fragment is underlined and bold
N regions are in red
105-16_23_sequenced with T7
Has 1 copy of amplified product in correct orientation GGNNNNNNNNNNGGNCNNNCCGCGGGAATTCGATT**CGACCACCACCCCAC
AGTATTACGATATTTTGGGGCCCTACTACTACGGTATGGACGTCTGGGGC
CAAGGGACCACGGTCACCGTCTCCTCAGGTAAGAATGGCCACTCTAGGG
CCTTTGTTTTCTGCTACTGCCTGTGGGGTTTCCTGAGCATTGCAGGTTGG
TCCTCGGGGCATGTTCCGAGGGGACCTGGGCA**ATCACTAGTGAATTCGCG
GCCGCCTGCAGGTCGACCATATGGGAGAGCTCCCAACGCGTTGGATGCATAG
CTTGAGTATTCTATAGTGTCACCTAAATAGCTTGGCGTAATCATGGTCATAGC
TGTTTCCTGTGTGAAATTGTTATCCGCTCACAATTCCACACAACATACGAGCC
GGAAGCATAAAGTGTAAAGCCTGGGGTGCCTAATGAGTGAGCTAACTCACAT
TAATTGCGTTGCGCTCACTGCCCGCTTTCCAGTCGGGAAACCTGTCGTGCCAN
CTGCATTAATGAATCGGCCAACGCGCGGGGAGAGGCGGTTTGCGTATTGGGC
GCTCTTCCGCTTCCTCGCTCACTGACTCGCTGCGCTCGGTCGTTCGGCTGCGGC
GAGCGGTATCNNNTCANTCAAAGGCGGTAATACGGTTATCCACAGAATCAGG
GGATAACGCAGGAAAGAACATGTGANCAAAAGGCCAGCAAAAGGCCAGGA
ACCGTAAAAAGGCCGCGTTGCTGGCGTTTTCCATAGGGCTCCGCCCCCTGA
CGAGCATCACAAAAATCGACGCTCAAGTCANAGGTGGCGAAACCCGACNGGA
CTANAAAGATANAGGCGTTTCCCNCCTGNAAANTCCCCTCGNGNGCTCTCNTG
TTCCGACCCTGCCGCTTTACCGNANNCNTGTTCNNCTTTCTNCCCTTCGGGAA
GCGNGNCGCTTTNCTCNTANNT (SEQ ID NO. 1)

METHOD OF ASSESSMENT

FIELD OF THE INVENTION

The present invention relates generally to a method of assessing the amplification efficiency of a primer and, more particularly, to a method of assessing either the relative or absolute efficiency of primers for use in quantitative PCR amplification. The method of the present invention is predicated on the assessment of primer efficiency relative to the Ct determined for a single target DNA molecule rather than Ct regression curve analysis of serially diluted samples. The provision of a much simpler yet more reliable method of determining primer efficiency is useful in a range of applications including, but not limited to, the diagnosis and/or monitoring of disease conditions which are characterised by specific gene sequences and the characterisation or analysis of specific gene regions of interest, in particular, the monitoring of disease conditions which are characterised by clonal lymphoid cell populations or disease conditions which are characterised by specific V(D)J recombination events (such as detecting minimal residual disease in leukaemias) and which require the use of patient specific primers.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-MQANT-003A.txt, the date of creation of the ASCII text file is Aug. 20, 2020, and the size of the ASCII text file is 3 KB.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification.

Bibliographic details of the publications referred to by author in this specification are collected alphabetically at the end of the description.

A clone is generally understood as a population of cells which has descended from a common precursor cell. Diagnosis and/or detection of the existence of a clonal population of cells or organisms in a subject has generally constituted a relatively problematic procedure. Specifically, a clonal population may constitute only a minor component within a larger population of cells or organisms. For example, in terms of the mammalian organism, one of the more common situations in which detection of a clonal population of cells is required occurs in terms of the diagnosis and/or detection of neoplasms, such as cancer. However, detection of one or more clonal populations may also be important in the diagnosis of conditions such as myelodysplasia or polycythaemia vera and also in the detection of antigen driven clones generated by the immune system.

Generally, the population within which the clone arises corresponds to a population of cells within a particular tissue or compartment of the body. Nevertheless, despite the fact that sampling such a population of cells effectively narrows the examination to a sub group of cells or organisms, this may nevertheless still present a clinician with a large background population of cells or organisms within which the clonal population must be identified.

If the members of the clone are characterized by a molecular marker, such as an altered sequence of DNA, then the problem of detection may be able to be translated into the problem of detecting a population of molecules which all have the same molecular sequence within a larger population of molecules which have a different sequence, either all being the same and different, or being heterogeneous to a greater or lesser extent. The level of detection of the marker molecules that can be achieved is very dependent upon the sensitivity and specificity of the detection method, but nearly always, when the proportion of target molecules within the larger population of molecules becomes small, the signal noise from the larger population makes it impossible to detect the signal from the target molecules. A specific class of molecular markers which, although highly specific, present unique complexities in terms of its detection are those which result from genetic recombination events.

Recombination of the genetic material in somatic cells involves the bringing together of two or more regions of the genome which are initially separate. It may occur as a random process but it also occurs as part of the developmental process in normal lymphoid cells.

In relation to cancer, recombination may be simple or complex. A simple recombination may be regarded as one in which two unrelated genes or regions are brought into apposition. A complex recombination may be regarded as one in which more than two genes or gene segments are recombined. The classical example of a complex recombination is the rearrangement of the immunoglobulin (Ig) and T-cell receptor (TCR) variable genes which occurs during normal development of lymphoid cells and which involves recombination of the V, D and J gene segments. The loci for these gene segments are widely separated in the germline but recombination during lymphoid development results in apposition of V, D and J gene segments, or V and J gene segments, with the junctions between these gene segments being characterised by small regions of insertion and deletion of nucleotides ($N_1$ and $N_2$ regions). This process occurs randomly so that each normal lymphocyte comes to bear a unique V(D)J rearrangement which may be a complete VDJ rearrangement or a VJ or DJ rearrangement, depending both on the gene which is rearranged and on the nature of the rearrangement. Since a lymphoid cancer, such as acute lymphoblastic leukaemia, chronic lymphocytic leukaemia, lymphoma or myeloma, occurs as the result of neoplastic change in a single normal cell, all of the cancer cells will, at least originally, bear the junctional V(D)J rearrangement originally present in the founder cell. Subclones may arise during expansion of the neoplastic population and further V(D)J rearrangements may occur in them.

The unique DNA sequences resulting from recombination and which are present in a cancer clone or subclone provide a unique genetic marker which can be used to monitor the response to treatment and to make decisions on therapy. Monitoring of the clone can be performed by PCR, flow cytometry or next-generation sequencing. Monitoring by flow cytometry involves the determination of the immunophenotype of the cancer cells at diagnosis and searching for the same phenotype in subsequent samples in order to detect and quantify the cancer cells. Next-generation sequencing is a newer approach, but is a costly technique.

PCR-based analysis is a preferred method due to its potentially high level of specificity and automation. Quantification by PCR conventionally involves sequencing of the marker rearrangement using DNA from a sample taken at the time of diagnosis, synthesis of patient-specific primers and use of these primers in a PCR on DNA extracted from samples obtained during treatment. Usually, two primers are placed on either side of the site of recombination, typically with the downstream primer being directed to the J gene segment and the upstream primer (which is also known as the allele specific oligonucleotide [ASO], being designed to be directed to the most variable region of the rearrangement (Brisco et al. 1991; Bruggemann et al, 2004; Pongers-Willemse et al, 1999; Nakao et al, 2000; van der Velden et al, 2002; van der Velden et al, 2004; van der Velden et al, 2007; van der Velden et al, 2009; van der Velden et al, 2014; Verhagen et al, 2000). Occasionally the upstream primer is directed to the V gene segment and the ASO primer is downstream and is directed to the most variable region of the rearrangement. The non-ASO primer is thus a consensus primer as it is directed to a conserved region which is common to many different rearrangements.

Monitoring by PCR of minimal residual disease (minimal residual disease, "MRD") in leukaemia has become widely used in clinical practice. Typically, decisions are made on whether to continue or change treatment by measuring the number of leukaemic cells (MRD) at the end of induction treatment (approximately one month) and after several cycles of consolidation treatment (approximately 80 days). A decision may be made to increase the intensity of treatment if the level of MRD at the end of induction is above a defined cut-off level. This cut-off level varies slightly between different group protocols but is typically between $10^{-3}$ (1/1000) and $10^{-4}$ (1/10,000) leukaemic cells/total cells.

Real-time quantitative polymerase chain reaction (RT-qPCR) is a widely used variant of PCR which is used to measure the number of molecules of a DNA target. Amplification is monitored serially using fluorescence, and the number of cycles to reach a defined fluorescence threshold (cycles to threshold, Ct) is noted. At the same time, a standard curve is constructed using a series of dilutions of a standard. Typically the various Cts from the standard curve approximate a straight line when plotted against the logarithm of the concentrations of the standard, and the concentration of the unknown target can be determined from the Ct of the target and the equation of the line of best fit for the standard curve.

Efficient amplification is important in general use of the PCR but is particularly important when the PCR is used in a quantitative fashion such as in RT-qPCR. It is also important when it is desired to avoid bias when using two different pairs of primers to amplify two different targets in the same reaction, or even when the same set of primers is used to amplify two different targets in the same reaction as is the case when next-generation sequencing is used to quantify minimal residual disease.

A third situation in which efficient amplification is important is when it is desired to have consistent and optimal performance of a variety of different primer pairs. This is only really possible when all of the primers are operating at close to maximum efficiency. An example of this situation is the use of patient-specific primers to quantify rearrangements of the immunoglobulin (Ig) or T cell receptor (TCR) genes. Quantification of these rearrangements is used to assess the level of residual disease in leukaemia, lymphoma and myeloma. The rearrangement in each patient is unique and as a consequence at least one of the two primers for the rearrangement is unique and specific for that patient only. As a consequence, determining and documenting the efficiency of the patient-specific primer is not straightforward. This uncertainty as to the efficiency of patient-specific primers has inhibited their routine and widespread use, particularly in the United States, for quantification of minimal residual disease.

Except for the terminal stage, PCR involves exponential amplification of the target. Progress is measured by fluorescence. At any point during exponential amplification, $$N = N_0 \cdot a^C$$

where $N_0$=the initial number of targets, N=the number of targets at the point of interest, a is the amplification/cycle and C is the number of cycles taken to reach that point. By calculating the logarithms of each side, this equation can also be expressed as:

$$\log_{10} N = \log_{10}(N_0) + C \cdot \log_{10}(a) \quad (1)$$

Theoretically it should be possible to determine amplification/cycle by determining the other three unknowns in the equation. However, although the determination of a precise value of C is straightforward, the determination of a precise value of $N_0$ is affected by imprecision in the measurement of DNA concentration and by any occurrence of DNA degradation. The latter will lead to the inability of targets to be amplified. Owing to these factors, the determination of a value of N is problematic.

At a certain point, the fluorescence reaches a fixed point, termed the threshold, where it is clearly above background and still exponentially increasing. If $N_t$ is the number of targets at threshold and $C_t$ is the number of cycles to reach threshold, then equation (1) can be expressed as:

$$C_t = \log_{10}(N_t)/\log_{10}(a) - \log_{10}(N_0)/\log_{10}(a)$$

For one pair of primers under constant conditions, the amplification efficiency is constant and, therefore:

$$Ct = \text{constant} - \log_{10}(N_0)/\log_{10}(a) \quad (2)$$

The relationship between Ct and $\log_{10}(N_0)$ is a straight line with the slope given by the relationship:

$$\text{slope} = -1/\log_{10}(a)$$

and $$a = 10^{-1/slope} \quad (3)$$

Amplification efficiency (E) is conventionally derived from the value of "a" by subtracting unity and expressing the result as a percentage. Thus:

$$E = a - 1$$

The value of E can be estimated using equation (1) but in addition to the limitations mentioned previously, this approach has also proved difficult owing to the limited range of exponential amplification which can be analysed which is above background but still exponential. At present amplification is almost universally analysed using equations (2) and (3). From equation (3):

$$E = 10^{-1/slope} - 1 \quad (4)$$

Thus, in practice, primer efficiency is conventionally determined by amplifying a range of concentrations of the target using quantitative PCR, determining the regression line between the logarithm of target concentration and the observed Ct values, and calculating primer efficiency using the equation (4).

When the observed slope is −3.322, the efficiency is 100% but this level of efficiency is rarely if ever achieved.

Unfortunately this method is not very precise and requires a large number of replicates and careful attention to detail. A standard curve, relating the Ct to the logarithm of input target, is usually performed as part of a routine RT-qPCR. However, it gives only a very general measure of amplification efficiency and exhibits both imprecision and wide variation in results. For example, slopes of the standard curve which have ranged from −3.1 to −3.9 have been regarded as acceptable when quantifying minimal residual disease (MRD) in leukaemia by PCR (van der Velden, 2007). These slopes correspond to efficiencies ranging from 110% to 80%.

Accordingly, there is an ongoing need to develop improved means of assessing primer efficiency. In work leading up to the present invention, it has been surprisingly determined that primer amplification efficiency can be more accurately and rapidly assessed, either relatively or absolutely, by reference to the mean Ct value which is determined from the amplification of a single target molecule in an assay which has been standardised to enable reference primers to amplify a single reference template molecule. Specifically, whereas conventional PCR theory teaches that primer efficiency should be assessed using serial dilutions to determine the Ct at each dilution point, followed by the plotting of a regression line of Ct vs the logarithm of the target DNA starting mass, it is also taught that quantitative amplification should not be performed using either highly concentrated or highly diluted samples of target DNA due to the errors which are routinely observed to occur. For example, if inhibitors are present in a concentrated sample of target DNA, more cycles are needed to cross the threshold of detection, thereby artificially increasing Ct. One mechanism to improve the curve slope is to dilute the sample since the inhibitors are diluted together with the target DNA. However, highly diluted samples are also generally recommended to be omitted from analysis due to the high variability, due to stochastic effects, which can be observed in the amplification results. Nevertheless, it has been surprisingly determined that amplification from a single target DNA copy is, in fact, highly accurate and produces a much lower coefficient of variation across multiple repeats than that observed where efficiency is determined using traditional Ct regression line modelling, this being entirely contrary to all current amplification teaching. When performed in the context of an assay which has been standardised, the efficiency of primer pairs can be quantitatively assessed, either relatively or absolutely, relative to the efficiency of the reference primers and nucleic acid template using the same optimised and standardised assay protocol. Still further, the efficiency of multiple primer sets can therefore also be directly compared to one another, to the extent that they are assessed under the same set of standardised conditions. Finally, it has been even more unexpectedly determined that the Ct results obtained from the amplification of a single copy of target DNA is so reliable, that whereas one would assume that when assessing the efficiency of primers directed to a specific gene or gene family, that this should be assessed relative to reference primers which are directed to a homologous gene or gene family template, one can in fact use an unrelated gene, such as the ubiquitously expressed GALT gene, as the reference template. More specifically, if a gene exhibiting little or no homology to the test primer targets of interest is used as the reference template in an optimised and standardised protocol of a quantitative PCR assay, this standardised assay will produce comparable results to a standardised assay which is performed using reference primers and template which exhibit a higher level of homology to the test primers and target of interest, thereby unexpectedly enabling the application of a given standardised assay to a substantially broader scope of primers requiring efficiency assessment than just those primers which exhibit homology to the selected reference primers and template.

These findings are both unexpected and counterintuitive. The development of this simple yet highly reliable means of assessing primer efficiency obviates the need to perform the time consuming and much more variable Ct regression line efficiency modelling every time the efficiency of a primer needs to be determined. Primer efficiency can now be quickly and much more accurately determined, either relatively or absolutely, and direct comparison between the efficiency of different primer sets can be directly made. The present invention therefore has a wide range of potential applications, including in the research setting where the issue of determining primer efficiency in the context of designing or optimising a quantitative PCR reaction is a crucial step but is, currently, labour intensive and can produce quite variable results. This invention also has application in the clinical setting, in terms of diagnostic and prognostic applications, such as minimum residual disease (MRD) analysis, where highly sensitive detection of very low copy number targets is required and variability in primer efficiency is not desirable. Still further, since MRD testing necessitates the generation and use of patient specific primers, a rapid and simple means of assessing the efficiency of newly generated primers and which provides a standardised result across all tests is highly valuable. The present method therefore overcomes currently existing limitations in relation to the assessment of primer amplification efficiency.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The present invention is not to be limited in scope by the specific embodiments described herein, which are intended for the purposes of exemplification only. Functionally-equivalent products, compositions and methods are clearly within the scope of the invention, as described herein.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

The subject specification contains nucleotide sequence information prepared using the programme PatentIn Version 3.1, presented herein after the bibliography. Each nucleotide sequence is identified in the sequence listing by the numeric indicator <210> followed by the sequence identifier (e.g. <210>1, <210>2, etc). The length, type of sequence (DNA, etc) and source organism for each nucleotide sequence are indicated by information provided in the numeric indicator fields <211>, <212> and <213>, respectively. Nucleotide sequences referred to in the specification are identified by the indicator SEQ ID NO: followed by the sequence identifier (e.g. SEQ ID NO:1, SEQ ID NO:2, etc.). The sequence identifier referred to in the specification correlates to the information provided in numeric indicator field <400> in the sequence listing, which is followed by the sequence identifier (e.g. <400>1, <400>2, etc.). That is SEQ ID NO:1 as detailed in the specification correlates to the sequence indicated as <400>1 in the sequence listing.

One aspect of the present invention is directed to a method of assessing the amplification efficiency of a forward and reverse primer pair directed to a nucleic acid region of interest, said method comprising:
  (i) contacting a nucleic acid sample with said forward and reverse primer pair wherein said nucleic acid sample is characterised by the presence of a single copy of the nucleic acid region of interest;
  (ii) amplifying the nucleic acid sample of step (i) in accordance with a standardised quantitative amplification protocol, which protocol has been standardised to effect the amplification of a single copy of a reference nucleic acid template molecule using a reference forward and reverse primer pair directed to said template molecule; and
  (iii) determining the Ct of the amplification reaction of step (ii) and assessing the amplification efficiency of said primers from said Ct value.

In another aspect there is provided a method of assessing the amplification efficiency of a forward and reverse primer pair directed to a DNA region of interest, said method comprising:
  (i) contacting a DNA sample with said forward and reverse primer pair wherein said DNA sample is characterised by the presence of a single copy of the DNA region of interest;
  (ii) amplifying the DNA sample of step (i) in accordance with a standardised quantitative amplification protocol, which protocol has been standardised to effect the amplification of a single copy of a reference DNA template molecule using a reference forward and reverse primer pair directed to said template molecule; and
  (iii) determining the Ct of the amplification reaction of step (ii) and assessing the amplification efficiency of said primers from said Ct value.

In one embodiment, said nucleic acid region of interest comprises a SNP, point mutation, hypermutation, chromosomal translocation, genomic gene segment rearrangement, DNA insertion, DNA deletion or breakpoint, such as a chromosomal breakpoint, a specific gene segment, a specific region, part or section of a gene or an intergenic region.

In another embodiment, said nucleic acid region of interest is the rearranged immunoglobulin (Ig) or T cell receptor (TCR) DNA, more particularly the rearranged V, D and/or J segments.

In accordance with this embodiment there is provided a method of assessing the amplification efficiency of a forward and reverse primer pair directed to one or more rearranged V, D or J gene segments, said method comprising:
  (i) contacting a DNA sample with said forward and reverse primer pair wherein said DNA sample is characterised by the presence of a single copy of said rearranged V, D or J gene segments;
  (ii) amplifying the DNA sample of step (i) in accordance with a standardised quantitative amplification protocol, which protocol has been standardised to effect the amplification of a single copy of a reference DNA template molecule using a reference forward and reverse primer pair directed to said template molecule; and
  (iii) determining the Ct of the amplification reaction of step (ii) and assessing the amplification efficiency of said primers from said Ct value.

In still another embodiment and in the context of V(D)J rearrangement, said nucleic acid region of interest corresponds to the DJ or VDJ rearrangements of IgH, TCR β or TCR δ. In another embodiment said nucleic acid region of interest corresponds to the VJ rearrangement of Igκ, Igλ, TCRα or TCRγ.

In yet another embodiment, said nucleic acid region of interest is a V gene segment region, such as a region predisposed to undergoing hypermutation and/or a J gene segment region encoding a portion of the CDR3.

In still yet another embodiment, said nucleic acid region of interest is directed to gene segment regions encoding all or some of the V leader sequence, IgH FR1, IgH FR2 or IgH FR3.

In a further embodiment there is provided a method of assessing the amplification efficiency of a forward and reverse primer pair directed to a DNA region of interest, said method comprising:
  (i) contacting a DNA sample with said forward and reverse primer pair wherein said DNA sample is characterised by the presence of a single copy of the DNA region of interest;
  (ii) amplifying the DNA sample of step (i) in accordance with a standardised quantitative PCR protocol, which protocol has been standardised to effect the amplification of a single copy of a reference DNA template molecule using a reference forward and reverse primer pair directed to said template molecule; and
  (iii) determining the Ct of the amplification reaction of step (ii) and assessing the amplification efficiency of said primers from said Ct value.

In another embodiment the amplicons produced by said quantitative PCR are detected using a non-specific fluorescent dyes that intercalate with double-stranded DNA. In another embodiment the amplicons produced by said quantitative PCR are detected using a sequence-specific DNA probe operably linked to a reporter molecule such as a fluorescent reporter.

In yet another embodiment, said reference nucleic acid template is a rearranged IgH gene or the TCR gene.

In still yet another embodiment, said reference nucleic acid template is a single copy gene, preferably the GALT gene.

In a related aspect of the present invention there is provided a method of determining the Ct of a forward and reverse primer pair directed to a nucleic acid region of interest, said method comprising:
  (i) contacting multiple nucleic acid samples with said forward and reverse primer pair wherein at least two of said multiple samples are characterised by the presence of a single copy of the nucleic acid region of interest;
  (ii) amplifying the nucleic acid samples of step (i) in accordance with a quantitative amplification protocol designed to effect the amplification of a single copy of a nucleic acid target molecule and determining the Ct of each aliquot; and
  (iii) determining the mean Ct of the amplification reactions of step (ii) which amplified from said single copy of the nucleic acid region of interest.

More particularly, there is provided a method of determining the Ct of a forward and reverse primer pair directed to a DNA region of interest, said method comprising:
  (i) performing a limiting dilution of a biological sample comprising said DNA region of interest and generating multiple aliquots of said sample wherein a subgroup of said aliquots contain no copies of said DNA region of interest;

(ii) contacting the aliquots of step (i) with said forward and reverse primer pair and amplifying said aliquots in accordance with a quantitative amplification protocol designed to effect the amplification of a single copy of said DNA region of interest and determining the Ct of each aliquot;

(iii) statistically determining the proportion of aliquots from step (i) comprising at least two starting copies of said DNA region of interest; and (iv) determining the mean Ct of the amplification reaction step (ii) wherein the calculation of said mean excludes the Ct results obtained both from aliquots in which no amplification was observed and the proportion of lowest individual aliquot Ct results corresponding to the proportion value determined in step (ii).

In accordance with the previous aspects of the invention, there is provided a method of assessing the amplification efficiency of a forward and reverse primer pair directed to a DNA region of interest, said method comprising:

(i) contacting multiple nucleic acid samples with said forward and reverse primer pair wherein at least two of said multiple samples are characterised by the presence of a single copy of the nucleic acid region of interest;

(ii) amplifying the DNA samples of step (i) in accordance with a standardised quantitative PCR protocol, which protocol has been standardised to effect the amplification of a single copy of a reference DNA template molecule using a reference forward and reverse primer pair directed to said template molecule; and (iii) determining the mean Ct of the amplification reactions of step (ii) and assessing the amplification efficiency of said primers from said Ct value.

In a further embodiment of this aspect, the mean Ct value of the test primers and/or the reference primers has been determined by:

a. performing a limiting dilution of a biological sample comprising said DNA region of interest and generating multiple aliquots of said sample wherein a subgroup of said aliquots contain no copies of said DNA region of interest;

b. contacting the aliquots of step (a) with said forward and reverse primer pair and amplifying the DNA of step (a) in accordance with said standardised quantitative PCR protocol and determining the Ct of each aliquot;

c. statistically determining the proportion of aliquots from step (a) comprising at least two starting copies of said DNA region of interest; and d. determining the mean Ct of the amplification reaction step (b) wherein the calculation of said mean excludes the Ct results obtained both from aliquots in which no amplification was observed and the proportion of lowest individual aliquot Ct results corresponding to the proportion value determined in step (b).

In one embodiment, said amplification efficiency is assessed relative to the efficiency point of reference determined from the amplification of the reference template DNA by the reference primers in the standardised assay.

In another embodiment, said efficiency point of reference is the mean Ct value of the reference primers and said amplification efficiency assessment is made by comparing the mean Ct value of the forward and reverse primer pair directed the DNA region of interest to the mean Ct value determined for the amplification of the reference forward and reverse primer pair directed to the reference DNA template molecule.

In yet another embodiment, said efficiency point of reference is $Nt_{(ref)}$ and said amplification efficiency assessment is made by using the mean Ct value of the forward and reverse primer pair directed the DNA region of interest $(Ct_{(test)})$ in the formula:

$$E_{(test)} = N_{t(ref)}^{1/Ct(test)} - 1$$

In still yet another embodiment, said efficiency point of reference is $E_{(ref)}$ and $C_{t(ref)}$ and said amplification efficiency assessment is made by using the mean Ct value of the forward and reverse primer pair directed the DNA region of interest $(Ct_{(test)})$ in the formula:

$$E_{(test)} = (E_{(ref)} + 1)^{Ct(ref)/Ct(test)} - 1$$

In another embodiment, said nucleic acid region of interest comprises a SNP, point mutation, hypermutation, chromosomal translocation, genomic gene segment rearrangement, DNA insertion, DNA deletion or breakpoint, such as a chromosomal breakpoint, a specific gene segment, a specific region, part or section of a gene or an intergenic region.

In still another embodiment, said nucleic acid region of interest is the rearranged immunoglobulin (Ig) or T cell receptor (TCR) DNA, more particularly the rearranged V, D and/or J segments.

In yet another embodiment and in the context of V(D)J rearrangement, said nucleic acid region of interest corresponds to the DJ or VDJ rearrangements of IgH, TCR β or TCR δ. In another embodiment said nucleic acid region of interest corresponds to the VJ rearrangement of Igκ, Igλ, TCRα or TCRγ.

In still yet another embodiment, said nucleic acid region of interest is a V gene segment region, such as a region predisposed to undergoing hypermutation and/or a J gene segment region encoding a portion of the CDR3.

In yet still another embodiment, said nucleic acid region of interest is directed to gene segment regions encoding all or some of the V leader sequence, IgH FR1, IgH FR2 or IgH FR3.

In a further embodiment, said amplification reaction is PCR.

In another further embodiment the amplicons produced by said quantitative PCR are detected using a non-specific fluorescent dyes that intercalate with double-stranded DNA. In another embodiment the amplicons produced by said quantitative PCR are detected using a sequence-specific DNA probe operably linked to a reporter molecule such as a fluorescent reporter.

In still another further embodiment, said reference nucleic acid template is a rearranged IgH gene or TCR gene.

In yet another further embodiment, said reference nucleic acid template is a single copy gene, preferably the GALT gene.

In a further aspect the present method is directed to a kit for facilitating assessment of the efficiency of a forward and reverse primer pair which are directed to a nucleic acid region of interest, said kit comprising a reference forward and reverse primer and instructions detailing the standardised amplification protocol method and/or minimum efficiency outcomes as herein before defined, optionally together with the reference nucleic acid template molecule as hereinbefore defined and reagent suitable for use in facilitating the amplification of the reference primers in accordance with the standardised protocol.

BRIEF DESCRIPTION OF THE DRAWINGS

FIG. 1 is a schematic representation illustrating that portion of the sequence of the plasmid that incorporates an IGH reference target. The sequence for the forward primer is CGACCACCACCCCACAGTATTACGATA (SEQ. ID NO: 2), the target sequence for the reverse J primer is ATGTTCCGAGGGGACCTGGGC (SEQ. ID NO: 3) and the inserted sequence is underlined and in bold. The EcoRI restrictions sites are shown in shading.

DETAILED DESCRIPTION OF THE INVENTION

Figure 2:
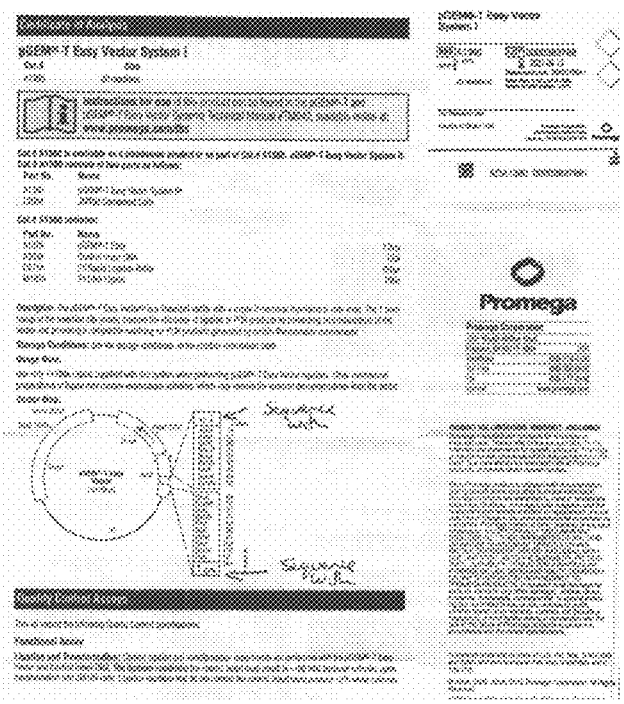
FIG. 2 shows information on the plasmid provided by the Manufacturer.

The present invention is predicated on the development of a simple means of reproducibly determining primer amplification efficiency with a high degree of accuracy by comparing their performance to that of reference primers. This development is enabled, in part, by the unexpected determination that primer efficiency is, in fact, precisely related to the Ct value which results from the standardised amplification of a single copy of a target molecule with that primer. By directly or indirectly assessing this test primer result relative to the efficiency of the reference primer amplification of a single copy of a nucleic acid template in the context of these standardised conditions, an accurate determination of the efficiency of the test primer can be established. This approach, rather than traditional Ct regression line modelling, has enabled the design of means for routine and reliable large scale primer efficiency testing. Where large numbers of primers are required to be tested, such as multiple sets of patient specific primers for use in MRD testing, the present method facilitates not only the simple and accurate determination of primer efficiency but, further due to the standardised nature of the assay protocol and, thereby, the results obtained therefrom, the direct comparison of efficiency between test primers is enabled. This is particularly desirable in circumstances where multiple different primers have been developed for a particular target and the most efficient primer is sought to be identified and used. In another example, one may now objectively determine whether a given primer pair are sufficiently efficient to be used in an application which requires a minimum level of efficiency. The method of the present invention is therefore useful in a wide range of research and clinical applications, in particular the design and testing of patient specific primers, such as for MRD testing in order to ensure that primers are sufficiently efficient to provide results which are sufficiently accurate to provide the basis for making treatment decisions.

Accordingly, one aspect of the present invention is directed to a method of assessing the amplification efficiency of a forward and reverse primer pair directed to a nucleic acid region of interest, said method comprising:
 (i) contacting a nucleic acid sample with said forward and reverse primer pair wherein said nucleic acid sample is characterised by the presence of a single copy of the nucleic acid region of interest;
 (ii) amplifying the nucleic acid sample of step (i) in accordance with a standardised quantitative amplification protocol, which protocol has been standardised to effect the amplification of a single copy of a reference nucleic acid template molecule using a reference forward and reverse primer pair directed to said template molecule; and
 (iii) determining the Ct of the amplification reaction of step (ii) and assessing the amplification efficiency of said primers from said Ct value.

Reference to a "nucleic acid" or "nucleotide" or "base" or "nucleobase" should be understood as a reference to both deoxyribonucleic acid or nucleotides and ribonucleic acid or nucleotides or purine or pyrimidine bases or derivatives or analogues thereof. In this regard, it should be understood to encompass phosphate esters of ribonucleotides and/or deoxyribonucleotides, including DNA (cDNA or genomic DNA), RNA or mRNA among others. The nucleic acid molecules of the present invention may be of any origin including naturally occurring (such as would be derived from a biological sample), recombinantly produced or synthetically produced. The nucleotide may also be a non-standard nucleotide such as inosine.

Reference to "derivatives" should be understood to include reference to fragments, parts, portions, homologs and mimetics of said nucleic acid molecules from natural, synthetic or recombinant sources. "Functional derivatives" should be understood as derivatives which exhibit any one or more of the functional activities of purine or pyrimidine bases, nucleotides or nucleic acid molecules. The derivatives of said nucleotides or nucleic acid sequences include fragments having particular regions of the nucleotide or nucleic acid molecule fused to other proteinaceous or non-proteinaceous molecules. The biotinylation of a nucleotide or nucleic acid molecules is an example of a "functional derivative" as herein defined. Derivatives of nucleic acid molecules may be derived from single or multiple nucleotide substitutions, deletions and/or additions. The term "functional derivatives" should also be understood to encompass nucleotides or nucleic acid exhibiting any one or more of the functional activities of a nucleotide or nucleic acid sequence, such as for example, products obtained following natural product screening.

"Analogs" contemplated herein include, but are not limited to, modifications to the nucleotide or nucleic acid molecule such as modifications to its chemical makeup or overall conformation or any other type of non-naturally occurring nucleotide. This includes, for example, modification to the manner in which nucleotides or nucleic acid molecules interact with other nucleotides or nucleic acid molecules such as at the level of backbone formation or complementary base pair hybridisation. Without limiting the present invention to any one theory or mode of action, nucleic acids are composed of three parts: a phosphate backbone, a pentose sugar, either ribose or deoxyribose and one of four bases. An analogue may have any of these altered. Typically the analogue bases confer, among other things, different base pairing and base stacking properties. Examples include universal bases, which can pair with all four canonical bases, and phosphate-sugar backbone analogues such as PNA, which affect the properties of the chain. Nucleic acid analogues are also called xeno nucleic acids. Non-naturally occurring nucleic acids include peptide nucleic acid (PNA), morpholino and locked nucleic acid (LNA), as well as glycol nucleic acid (GNA) and threose nucleic acid (TNA). Each of these is distinguished from naturally occurring DNA or RNA by changes to the backbone of the molecule.

The nucleic acid sample of interest and/or the template nucleotide sequence may be DNA or RNA or derivative or analogue thereof. Said nucleic acid may take the form of genomic DNA, cDNA which has been generated from an mRNA transcript, DNA generated by nucleic acid amplification, synthetic DNA or recombinantly generated DNA. If the subject nucleic acid sample is RNA, it would be appreciated that it will first be necessary to reverse transcribe the RNA to DNA, such as using RT-PCR. The subject RNA may be any form of RNA, such as mRNA, primary RNA transcript, ribosomal RNA, transfer RNA, micro RNA or the like. Preferably, said nucleic acid is DNA.

According to this embodiment there is provided a method of assessing the amplification efficiency of a forward and reverse primer pair directed to a DNA region of interest, said method comprising:
(i) contacting a DNA sample with said forward and reverse primer pair wherein said DNA sample is characterised by the presence of a single copy of the DNA region of interest;
(ii) amplifying the DNA sample of step (i) in accordance with a standardised quantitative amplification protocol, which protocol has been standardised to effect the amplification of a single copy of a reference DNA template molecule using a reference forward and reverse primer pair directed to said template molecule; and
(iii) determining the Ct of the amplification reaction of step (ii) and assessing the amplification efficiency of said primers from said Ct value.

Reference to a "nucleic acid region of interest" (herein also interchangeably referred to as a "target" region or sequence) should be understood as a reference to any DNA or RNA sequence which is sought to be analysed. This may be a gene, part of a gene, such as a gene segment or gene region, or an intergenic region. To this end, reference to "gene" should be understood as a reference to a DNA molecule which codes for a protein product, whether that be a full length protein or a protein fragment. In terms of chromosomal DNA, the gene will include both intron and exon regions. However, to the extent that the nucleic acid sample is cDNA, such as might occur if the target nucleotide sequence is vector DNA or reverse transcribed mRNA, there may not exist intron regions. Such DNA may nevertheless include 5' or 3' untranslated regions. Accordingly, reference to "gene" herein should be understood to encompass any form of DNA which codes for a protein or protein fragment including, for example, genomic DNA and cDNA. The subject target nucleotide sequence may also correspond to a non-coding portion of genomic DNA which is not known to be associated with any specific gene (such as the commonly termed "junk" DNA regions). It may correspond to any region of genomic DNA produced by recombination, either between two regions of genomic DNA or a region of genomic DNA and a region of foreign DNA such as a virus or an introduced sequence. It may also correspond to a region which may encompass a SNP, point mutation, hypermutation, chromosomal translocation, genomic gene segment rearrangement, DNA insertion, DNA deletion or breakpoint, such as a chromosomal breakpoint, a specific gene segment, a specific region, part or section of a gene, intergenic region or the like. The target sequence may also correspond to a region of a partly or wholly synthetically or recombinantly generated nucleic acid molecule. The subject target sequence may also be a region of DNA which has been previously amplified by any nucleic acid amplification method, including polymerase chain reaction (PCR) (i.e. it has been generated by an amplification method).

In one embodiment, said nucleic acid region of interest comprises a SNP, point mutation, hypermutation, chromosomal translocation, genomic gene segment rearrangement, DNA insertion, DNA deletion or breakpoint, such as a chromosomal breakpoint, a specific gene segment, a specific region, part or section of a gene or an intergenic region.

In another embodiment, said nucleic acid region of interest is the rearranged immunoglobulin (Ig) or T cell receptor (TCR) DNA, more particularly the rearranged V, D and/or J gene segments.

In accordance with this embodiment there is provided a method of assessing the amplification efficiency of a forward and reverse primer pair directed to one or more rearranged V, D or J gene segments, said method comprising:
(i) contacting a DNA sample with said forward and reverse primer pair wherein said DNA sample is characterised by the presence of a single copy of said rearranged V, D or J gene segments;
(ii) amplifying the DNA sample of step (i) in accordance with a standardised quantitative amplification protocol, which protocol has been standardised to effect the amplification of a single copy of a reference DNA template molecule using a reference forward and reverse primer pair directed to said template molecule; and
(iii) determining the Ct of the amplification reaction of step (ii) and assessing the amplification efficiency of said primers from said Ct value.

Without limiting the present invention to any one theory or mode of action, the Ig variable region encoding genomic DNA which may be rearranged includes the variable regions associated with the heavy chain or the κ or λ light chain while the TCR variable region encoding genomic DNA which may be rearranged include the α, β, γ and δ chains. In this regard, a cell should be understood to fall within the scope of a "lymphoid cell" provided the cell has rearranged the variable region encoding DNA of at least one immunoglobulin or TCR gene segment region. It is not necessary that the cell is also transcribing and translating the rearranged DNA. In this regard, "lymphoid cell" includes within its scope, but is in no way limited to, immature T and B cells which have rearranged the TCR or Ig variable region gene segments but which are not yet expressing the rearranged chain (such as TCR⁻ thymocytes) or which have not yet rearranged both chains of their TCR or Ig variable region gene segments. This definition further extends to lymphoid-like cells which have undergone at least some TCR or Ig variable gene region rearrangement but which cell may not otherwise exhibit all the phenotypic or functional characteristics traditionally associated with a mature T cell or B cell.

It should also be understood that although in one embodiment the subject rearrangement is a completed rearrangement, such as the completed rearrangement of at least one variable gene region, in another embodiment the subject rearrangement is a partial rearrangement. For example, a B cell which has only undergone the DJ recombination event is a cell which has undergone only partial rearrangement. Complete rearrangement will not be achieved until the DJ recombination segment has further recombined with a V segment. The primers of the present invention can therefore be designed to screen the partial or complete variable region rearrangement of the TCR or Ig chain.

Without limiting the present invention to any one theory or mode of action, V(D)J recombination in organisms with an adaptive immune system is an example of a type of site-specific genetic recombination that helps immune cells rapidly diversify to recognise and adapt to new pathogens. Each lymphoid cell undergoes somatic recombination of its germ line variable region gene segments (either V and J, D and J or V, D and J segments), depending on the particular gene segments rearranged, in order to generate a total antigen diversity of approximately $10^{16}$ distinct variable region structures. In any given lymphoid cell, such as a T cell or B cell, at least two distinct variable region gene segment rearrangements are likely to occur due to the rearrangement of two or more of the two chains comprising the TCR or Ig molecule, specifically, the α, β, γ or δ chains of the TCR and/or the heavy and light chains of the Ig molecule. In addition to rearrangements of the VJ, DJ or VDJ segment of any given Ig or TCR gene, nucleotides are randomly removed and/or inserted at the junction between the segments. This leads to the generation of enormous diversity.

The loci for these gene segments are widely separated in the germline but recombination during lymphoid development results in apposition of a V, D and/or J gene, with the junctions between these genes being characterised by small regions of insertion and deletion of nucleotides. This process occurs randomly so that each normal lymphocyte comes to bear a unique V(D)J rearrangement. Since a lymphoid cancer, such as acute lymphoblastic leukaemia, chronic lymphocytic leukaemia, lymphoma or myeloma, occurs as a result of neoplastic change in a single normal cell, all of the cancer cells will, at least originally, bear the junctional V(D)J rearrangement originally present in the founder cell. Subclones may arise during expansion of the neoplastic population and further V(D)J rearrangements may occur in them.

Reference to a "gene segment" should be understood as a reference to the V, D and J regions of the Ig and T cell receptor genes. The V, D and J gene segments are clustered into families. For example, there are 52 different functional V gene segments for the κ Ig light chain and 5 J gene segments. For the Ig heavy chain, there are 55 functional V gene segments, 23 functional D gene segments and 6 J gene segments. Across the totality of the Ig and T cell receptor V, D and J gene segment families, there are a large number of individual gene segments, thereby enabling enormous diversity in terms of the unique combination of V(D)J rearrangements which can be effected. For the sake of clarity, the rearranged Ig or T cell receptor [V(D)J] variable nucleic acid region will be referred to herein as a rearranged "gene" and the individual V, D or J nucleic acid regions will be referred to as "gene segments". Accordingly, the terminology "gene segment" is not exclusively a reference to a segment of a gene. Rather, in the context of Ig and TCR gene rearrangement, it is a reference to a gene in its own right with these gene segments being clustered into families. A "rearranged" Ig or T cell receptor variable region gene should be understood herein as a gene in which two or more of one V segment, one J segment and one D segment (if a D segment is incorporated into the particular rearranged variable gene in issue) have been spliced together to form a single rearranged "gene". In fact, this rearranged "gene" is actually a stretch of genomic DNA comprising one V gene segment, one J gene segment and one D gene segment which have been spliced together. It is therefore sometimes also referred to as a "gene region" since it is actually made up of 2 or 3 distinct V, D or J genes (herein referred to as gene segments) which have been spliced together. The individual "gene segments" of the rearranged immunoglobulin or T cell receptor gene are therefore defined as the individual V, D and J genes. These genes are discussed in detail on the IMGT database. The term "gene" will be used herein to refer to the rearranged Ig or T cell receptor variable gene. The term "gene segment" will be used herein to refer to the V, D and J segments. However, it should be noted that there is significant inconsistency in the use of "gene"/"gene segment" language in terms of Ig and T cell receptor rearrangement. For example, the IMGT refers to individual V, D and J "genes", while some scientific publication refers to these as "gene segments". Some sources refer to the rearranged variable Ig or T cell receptor as a "gene region" while others refer to it as a "gene". The nomenclature which is used in this specification is as defined earlier.

Still without limiting the present invention to any one theory or mode of action, the nature of genetic recombination events is such that a junction between the recombined genes or gene segments (as defined herein) may be characterised by the deletion and insertion of random nucleotides resulting in the formation of "N regions". These N regions are also unique and are themselves sometimes therefore useful targets in the context of target sequence analysis. Accordingly, it is generally understood that the V(D)J rearrangement provides combinatorial diversity while the addition of N nucleotides or palindromic (P) nucleotides provides junctional diversity.

It should also be understood that within the context of V(D)J rearrangement, the secondary structure of the protein molecule which is translated does itself comprise unique features which are themselves often the subject of analysis, albeit it in terms of the DNA sequence regions within the V(D)J rearrangement which encode these secondary structure features. For example, the translated variable region of IgH (the Ig heavy chain) or the TCR β or δ chains takes the form of three looped hypervariable regions which are usually referred to as the complementary determining regions (CDR) 1, 2 and 3. These CDR regions are flanked by four framework regions (FR) 1, 2, 3 and 4. Without limiting the present invention to any one theory or mode of action, the V gene segment is understood to encode the CDR1, CDR2, leader sequence, FR1, FR2 and FR3. The CDR3 region is encoded by part of the V gene segment, all of the D gene segment and part of the J gene segment. The remainder of the J gene segment generally encodes FR4.

Accordingly, in one embodiment and in the context of V(D)J rearrangement, said nucleic acid region of interest corresponds to the VJ, DJ or VDJ rearrangements of IgH, TCR β or TCR δ. In another embodiment said nucleic acid region of interest corresponds to the VJ rearrangement of Igκ, Igλ, TCRα or TCRγ.

In yet another embodiment, said nucleic acid region of interest is a V gene segment region, such as a region predisposed to undergoing hypermutation and/or a J gene segment region encoding a portion of the CDR3.

In still yet another embodiment, said nucleic acid region of interest is directed to gene segment regions encoding all or some of the V leader sequence, IgH FR1, IgH FR2 or IgH FR3.

The method of the present invention is directed to determining the amplification efficiency of a primer pair. By "amplification efficiency" is meant the increase in amplicons per amplification cycle. This is commonly expressed as the percentage increase in the number of target gene molecules at the end of a PCR cycle in relation to the number of target molecules at the beginning of the same PCR cycle. Ideally, the number of molecules of a target sequence should double during each replication cycle, this corresponding to a 100% amplification efficiency. However, this is rarely the case. Without limiting the present invention to any one theory or mode of action, the causes of amplification efficiency of less than 100% can include one or more of poor primer design, non-optimal reagent concentrations or non-optimal reaction conditions. Secondary structure formations such as dimers and hairpins or inappropriate melting temperatures (Tm) can also affect primer template annealing thereby resulting in poor amplification. It would be appreciated by the skilled person that since the method of the present invention is predicated upon testing forward and reverse primer pairs in a standardised amplification system, the efficiency of the primer itself will be the only significant variable and the result obtained from the application of the present method will therefore reflect the efficiency of the primer itself and not some other component of the assay. Accordingly, the reference to "amplification efficiency of a forward and reverse primer pair" herein is a reference to the amplification efficiency achievable using a particular primer pair and is not intended as a reference to the contribution to amplification efficiency of any other component of the subject amplification reaction. It should also be understood that discussion herein of "primer efficiency" is simply an interchangeable reference to the amplification efficiency of the primer pair which is tested according to the method of the present invention. It should also be understood that although the method of the present invention provides the amplification efficiency of a forward and reverse primer pair, this method also enables the calculation of the relative contribution to that efficiency result of either the forward or reverse primer alone. As discussed in more detail hereafter, the present method lends itself to potentially selecting for use, in the context of the test primer pair, one of the reference primers. Since the efficiency of the reference primers is known, and the only difference between the reference primer assay and the test primer assay is the fact that one of the reference primers (either the forward primer or the reverse primer) is replaced with a test primer, the efficiency result obtained from the test primer assay, when assessed relative to the efficiency point of reference determined using the reference primer pair, will effectively provide a readout of the impact to efficiency of the single test primer which was used to replace one of the reference primers.

Reference to a "primer" or an "oligonucleotide primer" should be understood as a reference to any molecule comprising a sequence of nucleotides, or functional derivatives or analogues thereof, the function of which includes hybridisation to a region of a nucleic acid molecule of interest (the DNA of interest interchangeably being referred to as a "target DNA"). It should be understood that the primer may comprise locked nucleic acid or non-nucleic acid components. For example, the primer may also comprise a non-nucleic acid tag such as a fluorescent or enzymatic tag or some other non-nucleic acid component which facilitates the use of the molecule as a probe or which otherwise facilitates its detection or immobilisation. The primer may also comprise additional nucleic acid components, such as the oligonucleotide tag which is discussed in more detail hereinafter. In another example, the primer may be a protein nucleic acid which comprises a peptide backbone exhibiting nucleic acid side chains. Preferably, said oligonucleotide primer is a DNA primer.

Reference to "forward primer" should be understood as a reference to a primer which amplifies the target DNA in the DNA sample of interest by hybridising to the antisense strand of the target DNA. Reference to "reverse primer" should be understood as a reference to a primer which amplifies the target DNA in the DNA sample of interest and in the PCR by hybridising to the sense strand of the target DNA. Reference to a "forward and reverse primer pair" should therefore be understood as a reference to a forward primer and a reverse primer which, together, will be tested in the method of the present invention. Accordingly, it would be appreciated that the amplification efficiency result which is obtained is indicative of the efficiency of the selected forward and reverse primers when used together. It should be understood that in some situations both the forward and the reverse primers will have been uniquely and specifically selected or designed for a particular application and will be tested to determine their amplification efficiency. However, in other situations, it may be that only one of the forward or reverse primers is required to be uniquely designed and the other primer may be a primer which is known and available, such as a consensus primer or commercially available primer, or even one of the reference primers which is used in the standardised amplification reaction (as discussed in more detail hereafter) to generate the efficiency point of reference against which the test primer Ct result is analysed. In this case, the efficiency result will still attach to the combination of primers but where one of the primers is the same in multiple primer pairs which are tested (such as a consensus J primer for an Ig V(D)J amplification but a unique V primer for each primer pair) and the same nucleic acid region of interest is amplified with all these primers, the efficiency result when compared as between these primer pairs which each use one common primer and one distinct primer will effectively provide substantial information in relation to the efficiency of the unique primer. This type of analysis may routinely occur in the context of MRD analysis of B and T cell neoplasia, for example, where primers directed to a specific V(D)J rearrangement are required to be used. In this situation, it is common for the rearrangement specificity (often commonly referred to as "patient specificity") to be provided by the V primer while the J primer which is selected for use may be a consensus or family primer which can be used in the context of a wide range of different patient rearrangements.

The design and synthesis of primers suitable for use in the present invention would be well known to those of skill in the art. In one embodiment, the subject primer is 4 to 60 nucleotides in length, in another embodiment 10 to 50 in length, in yet another embodiment 15 to 40 in length, in still another embodiment 20 to 35 in length. In yet still another embodiment, primer is about 25, 26, 27, 28, 29, 30, 31, 32, 33 or 34 nucleotides in length.

The amplification protocol of the present invention is a quantitative amplification reaction. Reference to a "quantitative" amplification reaction is a reference to an amplification reaction which monitors the amplification of a target DNA molecule during the amplification reaction in real time and not at the end of the reaction, as is typical for classical polymerase chain reaction (PCR) or digital PCR. Nevertheless, it should be noted that with some digital PCR instruments it is also possible to perform real-time monitoring and to determine the Ct values resulting from amplification of single target templates. Quantitative PCR (qPCR) is also commonly referred to as real time PCR (RT-PCR) or real time quantitative PCR (RT-qPCR). In this regard, RT-PCR is also the abbreviation used to describe reverse transcriptase PCR. However, to the extent that RT-PCR may be referenced herein, it is intended as a reference to quantitative (real time) PCR.

Still without limiting the present invention in any way, two common methods for the detection of PCR products in real-time PCR are (1) non-specific fluorescent dyes that intercalate with any double-stranded DNA, such as SYBR Green, EvaGreen and Syto 82 and (2) sequence-specific DNA probes consisting of oligonucleotides that are labelled with a fluorescent reporter such as fluorescein, Hex or Texas Red, which permit detection only after hybridisation of the probe with its complementary sequence.

In one embodiment, said amplification reaction is PCR.

According to this embodiment there is provided a method of assessing the amplification efficiency of a forward and reverse primer pair directed to a DNA region of interest, said method comprising:
(i) contacting a DNA sample with said forward and reverse primer pair wherein said DNA sample is characterised by the presence of a single copy of the DNA region of interest;
(ii) amplifying the DNA sample of step (i) in accordance with a standardised quantitative PCR protocol, which protocol has been standardised to effect the amplification of a single copy of a reference DNA template molecule using a reference forward and reverse primer pair directed to said template molecule; and
(iii) determining the Ct of the amplification reaction of step (ii) and assessing the amplification efficiency of said primers from said Ct value.

In another embodiment the amplicons produced by said quantitative PCR are detected using a non-specific fluorescent dye that intercalates with double-stranded DNA. In another embodiment the amplicons produced by said quantitative PCR are detected using a sequence-specific DNA probe operably linked to a reporter molecule such as a fluorescent reporter.

As detailed hereinbefore, the method of the present invention is predicated on the determination that the Ct value which is obtained when a single copy of a target molecule is amplified provides a more accurate and consistent readout of amplification efficiency than the traditional Ct regression line modelling method which is currently recommended to be performed. Without limiting the present invention to any one theory or mode of action, Ct regression line modelling is based on determining the Ct from a series of serially diluted target DNA concentrations. These Ct values are then plotted on a logarithmic scale of starting DNA concentration. The slope of the regression line enables calculation of the amplification reaction. However, the coefficient of variation of the amplification efficiency is substantially greater when calculated using Ct regression line modelling than when the Ct of a single starting copy of target DNA is determined. In terms of calculating the efficiency of a quantitative amplification reaction in accordance with the present method, and by extension the efficiency of the primer, the subject reaction must be standardised such that the variables which could impact on amplification efficiency, other than the primers and target DNA, are substantially equivalent. In this regard, reference to "standardised" or "standardisation" in the context of the subject amplification protocol should be understood as a reference to those elements of the amplification protocol, other than the design of the primers and selection of target DNA, exhibiting functional equivalency as between the subject reference and test primer amplification reactions. By "functional equivalency" is meant that the subject elements, as described further below, even if not actually identical, nevertheless deliver equivalent functional outcomes. For examples, one may elect to use two different types of reagents as between the reference and test primer amplification reactions, which reagents, although different in terms of chemical composition and/or source, nevertheless exhibit identical functional activity. In another example, one may elect to use two different instruments provided that both instruments enable the generation of identical reaction conditions. If so, the amplification reactions which use these instruments would be regarded as standardised. Examples of factors which are standardised include, but are not limited to, reagent components and materials (e.g. reagent concentrations and materials for detecting amplification product in real time, such as intercalating dyes or sequence specific reporter labelled probes), methodology (e.g. reaction volume, Tm, cycling conditions and other reaction conditions), the means selected to monitor amplification and determine Ct value, instrumentation and settings (such as the threshold line setting) and the like. Accordingly, any amplification reaction which is a standardised reaction in accordance with the present method will be performed according to a defined set of parameters such that the only significant variables in the reaction are the selection of the target DNA and the design of the forward and reverse primer pair which will be used in the reaction to amplify the DNA region of interest. Where it may be determined that it is desirable to diverge from the standardised reaction protocol for a particular test primer, it will be necessary to recalibrate the reference primers under these new reaction conditions such that the Ct value obtained from the test primers can be analysed against a reference primer result which has been generated under the same reaction conditions as those used to amplify the test primers. The test primer results cannot be assessed against the original reference primer results which were generated under a different set of reaction conditions.

In one embodiment, the standardised amplification protocol which is applied to the reference and test primers is identical.

The quantitative PCR protocol which is used in the method of the invention is one which has been designed to effect the amplification of a single copy of a reference nucleic acid template molecule. By "single copy" is meant a single copy of the subject template molecule, which molecule is then subjected to amplification in accordance with the method of the present invention. Reference to "single copy" in the context of the nucleic acid region of interest should be understood to have a corresponding meaning. It should be understood that in terms of designing an amplification protocol which will reliably and reproducibly amplify a single copy of a reference nucleic acid template molecule, and will thereby become the standard which is used in accordance with the present invention, this may be achieved either by establishing standardised conditions using the reference primers together with their target nucleic acid template or by using any other suitable primer pair and target nucleic acid, provided that the standardised conditions are determined to be appropriate to amplify a single copy of target DNA using the reference and test primers of interest.

The standardised amplification protocol is performed using a reference forward and reverse primer pair which are directed to amplifying a reference nucleic acid template molecule. By "reference" primer or "reference" template nucleic acid is meant the primers and nucleic acid target which are used to establish the Ct, Nt and/or amplification efficiency point of reference (referred to herein as an "efficiency point of reference" or an "efficiency benchmark") against which the test primer amplification results will be assessed. In this regard, a "reference nucleic acid template" is the nucleic acid molecule which the reference primer is designed to amplify. This is different to the earlier defined "nucleic acid region of interest" ("target nucleic acid") which the primers that are the subject of efficiency analysis by the present method are directed to. In general, the reference template molecules do not directly correspond to a nucleic acid region of interest molecule, although this possibility is not excluded, but they may be designed or selected such that they exhibit structural or sequence homology to the classes of molecules which are to be the subject of testing. For example, in the context of analysis of the efficiency of patient-specific primers directed to a specific IgH V(D)J rearrangement, one might elect to select a rearranged IgH sequence as the reference template sequence, together with appropriate reference primers, such as either consensus primers or gene segment family primers directed to the V region and the J region of the selected rearrangement. A different set of reference primers and reference template may be used in the context of a standardised assay for use with a different class of test primer pair and target, such as a gene breakpoint region. In this regard, it would be appreciated that for every set of reference primers which may be selected for use with respect to a particular class of test primers, the efficiency point of reference will have to be determined for each set of reference primers which the skilled person may choose to use for the analysis of a particular class of test primers. In this regard, in one embodiment the skilled person may determine that a primer that was originally analysed as a test primer would, in fact, lend itself to being used as the reference primer and would thereby replace the use of the original reference primer. In this situation, regardless of whether the test primer which will be newly used as a reference primer is to be amplified under the same standardised conditions as the original reference primer or under a different set of standardised conditions, the new reference primer will have to be tested under the selected standardised conditions and its Ct, Nt and/or amplification efficiency determined in order to establish the new efficiency point of reference against which future test primers will be assessed. In another example, if it is desired to diverge from the recommended standardised conditions for a given reference primer pair, for example to enable the use of different amplification conditions (eg. changes to amplification medium constituents), different methodology (eg. use of alternative probes or fluorochromes for monitoring amplification) or different instrumentation to that used originally, it will be necessary to determine the efficiency point of reference results for the reference primer under these changed reaction conditions and then analyse the amplification efficiency of the test primers under these new conditions in order to enable the test primer results to be assessed relative to the new reference primer benchmark results.

The reference primer amplification reaction does not need to be performed contemporaneously with every test primer amplification which is performed under the same set of standardised conditions, although this is often the preferred situation. Rather, the original efficiency benchmark results of the reference primer, which were obtained at an earlier point in time, may be used as the standard against which all future test primer results are later assessed ("calibrated"), provided that the test primer results were obtained using the same standardised protocol under which the reference primer results were generated.

It should also be understood that the present invention extends to the use of a reference primer in the assay which is determining the efficiency of a test primer. For example, and as hereinbefore described, one may only require one unique primer for a particular nucleic acid region of interest if the specificity for that region can be provided by either the forward primer or the reverse primer alone. In this situation, and depending on the nature of the reference primers and reference template which were used to establish the efficiency point of reference in the standardised amplification protocol for the test primer of interest, one may be able to pair one of the reference primers with the test primer in issue, such as where the reference primers are consensus primers which are suitable to target and amplify the nucleic acid region of interest and the test primer is the unique primer providing the necessary specificity.

It is well within the skill of the person in the art to design or select appropriate reference primers and templates for use in the context of a standardised amplification protocol and, further, to determine across what scope of test primers and corresponding nucleic acid regions of interest this standardised protocol and reference primer combination can be used, bearing in mind that the amplification efficiency, Nt and/or Ct from the amplification of a single copy of a reference DNA template will establish the efficiency point of reference against which the Ct of the test primer assay will be either relatively or absolutely assessed. To this end, it has been surprisingly determined by the present inventors that, in fact, the method of the invention is effective even where the standardised assay is performed using a reference template molecule which exhibits little or no homology to the nucleic acid region of interest. For example, it has been determined that targeting any V, D and/or J gene recombination, whether T or B cell originating, together which any primer pair that will achieve amplification of the template rearrangement is effective to provide the efficiency point of reference required to enable the assessment of the amplification efficiency of test primers directed to any V(D)J rearrangement. In fact, it has been further determined that where an assay is optimised and standardised to exhibit a high level of efficiency using a reference template with no homology to the nucleic acid region of interest, such as the ubiquitously expressed GALT gene, the application of these standardised conditions, and the efficiency point of reference determined thereby to the assessment of the efficiency of the test primers nevertheless achieves an accurate efficiency assessment of the test primers, despite the fact that conventional teaching suggests that the nature of the target sequence which is amplified can itself contribute to variation in amplification efficiency. The use of primers directed towards a single copy gene, such as the GALT gene, to provide a reference system for the testing of primers directed towards other single copy genes has the advantage that the reference template is generally available and the masses of reference and test templates are the same if reference and test primers are compared in the same template. It would therefore be appreciated that the present method extends to either performing a standardised assay using a gene such as the GALT gene and performing all amplification efficiency testing of primers relative to this standard or establishing multiple different standardised assays which are each directed to testing the efficiency of primers directed to nucleic acid regions of interest which exhibit homology to the particular reference template used in the context of a given standardised assay.

In one embodiment, said reference nucleic acid template is a rearranged IgH or TCR sequence.

In another embodiment, said reference nucleic acid template is a single copy gene, in particular the GALT gene.

It would be appreciated that the quantitative PCR protocol may be standardised by any suitable mean which would be well known to the skilled person. Without limiting the present invention in any way, in one embodiment the protocol is standardised such that it is performing at a high level of efficiency, that is, it has been optimised for the primers to perform at a high level/maximal amplification efficiency. Achieving such optimisation usually necessitates optimising the reaction conditions, the method of monitoring amplification and determining the Ct value and the choice of instrumentation. Nevertheless, although in most cases the subject assay will be optimised to run at the highest level of efficiency which is achievable, there may situations in which although the subject assay has been standardised, these standardised conditions are not necessarily optimal. Since the test primers which are assessed in accordance with the present method are assessed using the standardised protocol, the efficiency of the standardised protocol provides the amplification efficiency point of reference, relative to which the test primer Ct results are analysed (calibrated). Accordingly, in an embodiment where achieving the best possible outcome in terms of identifying highly efficient primers is sought, establishing a standardised protocol which functions at a high level of efficiency is desirable.

The method of the present invention enables the relative or absolute determination of the efficiency of a test primer pair by amplifying, in accordance with the standardised PCR protocol, the test primers together with a single copy of the nucleic acid region of interest. The Ct value which is determined thereby can then be assessed relative to the amplification efficiency of the standardised reference primer assay, as determined using an initial Ct regression line modelling analysis of the reference primer assay, as further discussed hereafter. Reference to "Ct" is a reference to the cycle threshold. Without limiting the present invention in any way, in quantitative PCR a positive reaction is detected by the accumulation of a positive signal, such as a fluorescence signal released from a specific probe or non-specific intercalating dye, which is generated in real time during each cycle of amplification. Accordingly, reference to Ct should be understood as a reference to the number of amplification cycles which are required for the signal to reach threshold. The minimal level of fluorescence at which background levels are clearly and reliably exceeded is referred to as the "threshold" and this threshold may be manually set by the skilled person or it may be automatically set by the software of the amplification system which is selected for use. Ct levels are therefore generally inversely proportional to the amount of target nucleic acid in a sample. Wherein the lower the Ct level, the greater the amount of starting target nucleic acid in the sample. However, the efficiency of the assay, as well as other assay variables, may also impact Ct values. Accordingly, although Ct is generally regarded as a relative measure of the nucleic acid target starting concentration in a sample, there are many factors which may impact the Ct value other than just the starting concentration of the target DNA.

In the context of the present invention, the variables which impact Ct are minimised by standardising the assay and performing the amplification of the test primers from a single starting copy of the DNA region of interest. The skilled person will also be aware that factors other than just the amplification efficiency of the reference primer or pair may influence the Ct value that is observed and hence the value of $N_t$. Among such factors are the volume of the reaction, the positioning of the threshold by the operator or by the software of the instrument, the method of measuring the level of fluorescence during the course of the PCR, and the nature of the instrument. That this assay structure in fact enables more accurate, simple and reproducible determination of the efficiency of the test primers based on the Ct value obtained from a single copy of DNA of interest is counter-intuitive when one considers the current teaching that qPCR amplification Ct analyses derived from highly diluted samples are unreliable and that such highly diluted samples should be omitted from analysis due to the high variability, caused by stochastic effects, which can be observed in the amplification results. Still further, it has been even more unexpectedly determined that the Ct result obtained from the amplification of a single copy of target DNA is so reliable, that whereas one would assume that when assessing the efficiency of primers directed to a specific gene or gene family, that this should be assessed relative to assay conditions which have been standardised using a homologous gene or gene family template, one can also use a non-homologous gene as the reference template and still obtain accurate efficiency results in relation to a test primer. These findings now obviate the need to perform Ct regression line analyses with respect to every test primer of interest, which regression lines exhibit a higher coefficient of variation than the method of the present invention, are more time consuming and laborious to perform and do not facilitate the assessment and direct comparison of the efficiency of multiple primer sets relative to one another since the prior art methods do not establish an objective efficiency point of reference against which all test primer Ct results can be assessed. Accordingly, prior art methods do not provide a means of objectively certifying primer efficiency in manner that provides certainty.

The present invention is therefore predicated upon amplifying, in accordance with a standardised protocol, a single copy of a nucleic acid region of interest with the forward and reverse primer pair of interest. Contacting the single copy of the nucleic acid region of interest with the forward and reverse primer pair should be understood as a reference to facilitating the mixing of the primer with said nucleic acid sample such that interaction (for example, hybridisation) can occur. Means of achieving this objective would be well known to those of skill in the art. Methods for achieving primer directed amplification are also very well known to those of skill in the art. It would also be appreciated by the skilled person that, for the reference primer, in order to maximise the accuracy of the amplification efficiency determination and the Ct observed when a single copy of the reference template is amplified, one may elect to perform multiple estimations of the amplification efficiency and single copy Ct and thereafter calculate the mean values in order to estimate the number of copies at threshold. It is also possible to obtain similar reference values by analysing, under standardised conditions, a population of primers and templates, performing single estimates of their amplification efficiency and single copy Ct, and from these determining the mean values of these statistics and calculating the mean this number of copies at threshold.

Reference to "nucleic acid sample" should be understood as a reference to either a biological or a non-biological sample. Examples of non-biological samples include, for example, the nucleic acid products of synthetically produced nucleic acid populations. Reference to a "biological sample" should be understood as a reference to any sample of biological material derived from an animal, plant or microorganism (including cultures of microorganisms) such as, but not limited to, cellular material, blood, mucus, faeces, urine, tissue biopsy specimens, fluid which has been introduced into the body of an animal and subsequently removed (such as, for example, the saline solution extracted from the lung following lung lavage or the solution retrieved from an enema wash), plant material or plant propagation material such as seeds or flowers or a microorganism colony. The biological sample which is tested according to the method of the present invention may be tested directly or may require some form of treatment prior to testing. For example, a biopsy sample may require homogenisation prior to testing or it may require sectioning for in situ testing. Further, to the extent that the biological sample is not in liquid form, (if such form is required for testing) it may require the addition of a reagent, such as a buffer, to mobilise the sample.

To the extent that the target DNA is present in a biological sample, the biological sample may be directly tested or else all or some of the nucleic acid material present in the biological sample may be isolated prior to testing. It is within the scope of the present invention for the target nucleic acid molecule to be pre-treated prior to testing, for example inactivation of live virus or being run on a gel. It should also be understood that the biological sample may be freshly harvested or it may have been stored (for example by freezing) prior to testing or otherwise treated prior to testing (such as by undergoing culturing).

The choice of what type of sample is most suitable for testing in accordance with the method disclosed herein will be dependent on the nature of the situation, such as the nature of the condition being monitored. For example, in a preferred embodiment a neoplastic condition is the subject of analysis. If the neoplastic condition is a leukaemia, a blood sample, lymph fluid sample or bone marrow aspirate would likely provide a suitable testing sample. Where the neoplastic condition is a lymphoma, a lymph node biopsy or a blood or marrow sample would likely provide a suitable source of tissue for testing. Consideration would also be required as to whether one is monitoring the original source of the neoplastic cells or whether the presence of metastases or other forms of spreading of the neoplasia from the point of origin is to be monitored. In this regard, it may be desirable to harvest and test a number of different samples from any one mammal. Choosing an appropriate sample for any given detection scenario would fall within the skills of the person of ordinary skill in the art.

The term "mammal" to the extent that it is used herein includes humans, primates, livestock animals (e.g. horses, cattle, sheep, pigs, donkeys), laboratory test animals (e.g. mice, rats, rabbits, guinea pigs), companion animals (e.g. dogs, cats) and captive wild animals (e.g. kangaroos, deer, foxes). Preferably, the mammal is a human or a laboratory test animal. Even more preferably the mammal is a human.

It would be appreciated, however, that since the method of the present invention requires that only a single copy of the nucleic acid region of interest is amplified, it will be necessary for the skilled person to prepare the subject sample such that only a single copy is present in the reaction. Means for achieving this would be well known to the skilled person and include, but are not limited to, the use of methods such as micro manipulation, deposition of individual cells into individual wells using flow cytometry and partitioning of individual cells into individual wells using limiting dilution.

In this regard, and in a related aspect of the present invention, it has been surprisingly determined that a reliable and accurate Ct result for the amplification of a single target nucleic acid molecule can be estimated by calculating a mean Ct value based on the application of a statistical analysis to the Ct results obtained from the amplification reactions which have been run on nucleic acid targets which have undergone serial dilution prior to amplification. This method obviates the need to identify and determine, with certainty, that a single target nucleic acid molecule has been successfully isolated and amplified, this being both time consuming and labour intensive. By having developed a method which enables a mean Ct result to be relied on based on statistically analysing results obtained from a straight forward limiting dilution assay, this has facilitated the application of the method of the present invention to large scale, automated analysis for determining primer efficiency.

The method of this aspect of the invention is based on the nucleic acid sample of interest being diluted across a series of reaction wells, or any other suitable compartmentalised or partitioned system, at a concentration such that only some of the reaction wells will contain one or more copies of the nucleic acid region of interest while the remaining wells will contain no copies of the nucleic acid region of interest. The probability that a given well will contain 0, 1, 2 or more starting copies of the nucleic acid region of interest is described by the Poisson distribution. Accordingly, by applying a Poisson distribution calculation, the number of wells containing two or more starting copies of DNA can be determined. Since a lower Ct will generally be associated with a higher starting concentration of target DNA, the lowest Ct results of the proportion of wells determined by the Poisson calculation to have contained two or more starting copies of the nucleic acid region of interest are discarded, as are the results of wells which showed no amplification, indicating that these wells contained no DNA. The Ct results of the remaining wells, which by virtue of the application of the Poisson distribution calculation are determined to have contained a single starting copy of the nucleic acid region of interest, are averaged in order to obtain a mean Ct value. The present inventor has determined that a mean Ct value calculated by this method is, in fact, a reliable estimate of the actual Ct of the amplification of a single starting copy of a target nucleic acid using a primer pair of interest and its confidence limits can be determined using standard statistical techniques.

Accordingly, in a related aspect of the present invention there is provided a method of determining the Ct of a forward and reverse primer pair directed to a nucleic acid region of interest, said method comprising:
  (i) contacting multiple aliquots of a nucleic acid sample with said forward and reverse primer pair wherein at least two of said multiple aliquots are characterised by the presence of a single copy of the nucleic acid region of interest;
  (ii) amplifying the nucleic acid aliquots of step (i) in accordance with a quantitative amplification protocol designed to effect the amplification of a single copy of a nucleic acid target molecule and determining the Ct of each aliquot; and
  (iii) determining the mean Ct of the amplification reactions of step (ii) which amplified from said single copy of the nucleic acid region of interest.

In one embodiment, said nucleic acid is DNA.

More particularly, there is provided a method of determining the Ct of a forward and reverse primer pair directed to a DNA region of interest, said method comprising:
  (i) performing a limiting dilution of a biological sample comprising said DNA region of interest and generating multiple aliquots of said sample wherein a subgroup of said aliquots contain no copies of said DNA region of interest;
  (ii) contacting the aliquots of step (i) with said forward and reverse primer pair and amplifying said aliquots in accordance with a quantitative amplification protocol designed to effect the amplification of a single copy of said DNA region of interest and determining the Ct of each aliquot;
  (iii) statistically determining the proportion of aliquots from step (i) comprising at least two starting copies of said DNA region of interest; and
  (iv) determining the mean Ct of the amplification reaction step (ii) wherein the calculation of said mean excludes the Ct results obtained both from aliquots in which no amplification was observed and the proportion of lowest individual aliquot Ct results corresponding to the proportion value determined in step (ii).

Reference to "mean" Ct should be understood as a reference to the average value where multiple separate amplification reactions were performed on a single starting copy of the nucleic acid region of interest. However, where the skilled person elects to perform only one amplification reaction on a single copy of the nucleic acid region of interest, the "mean" will simply correspond to the single Ct value which is obtained. It would be appreciated by the skilled person that the mean Ct value may be determined by any suitable experimental design and that the Poisson distribution based method hereinbefore described merely exemplifies one possibility.

Reference to "multiple" samples should be understood as a reference to 2 or more samples. Without limiting the invention in any way, said multiple samples are generated by performing a limiting dilution of a single starting sample of nucleic acid in order to generate multiple aliquots. By "aliquot" is meant a sample that is divided from the original sample, and which samples may also be diluted during this process. The subject aliquots are then maintained and amplified in separate reactions. The means by which these aliquots are partitioned may take any suitable form such as via the use of individual tubes or multiwell plates. In one embodiment the mean Ct value is determined from the Ct results of at least two nucleic acid aliquots which are characterised by the presence of only one copy of the nucleic acid region of interest prior to commencement of the amplification method of the present invention. In another embodiment, the limiting dilution of step (i) is designed to generate 2-384 aliquots, in another embodiment 8-96 aliquots and in yet another embodiment 12, 16 or 24 aliquots. In still yet another embodiment the number of aliquots corresponds to the number of partitioned samples generated during the course of a digital PCR. In this regard, means of performing a limiting dilution would be well known to the person of skill in the art.

It should be understood that the step of statistically determining the proportion of aliquots comprising two or more starting copies of target DNA may be performed at any suitable point in time and is not necessarily strictly calculated after the amplification step. That is, one may also perform this calculation immediately after the limiting dilution step is performed.

This aspect of the present invention is useful in a range of applications for any primer pair which may be the subject of interest and wherein the Ct of a single copy of target DNA is required. For example, one may combine the results obtained by this method together with the amplification efficiency determined using traditional regression line analysis to determine the number of amplified molecules which are generated at threshold for a particular primer pair of interest. This may find particular utility as a stand-alone method in terms of analysing the suitability of primers for use as reference primers. Alternatively, this method of determining Ct may be combined with, and used in the context of, the determination of the absolute or relative efficiency of a test primer relative to a reference primer, as described hereinbefore.

According to this embodiment there is provided a method of assessing the amplification efficiency of a forward and reverse primer pair directed to a DNA region of interest, said method comprising:
(i) contacting multiple nucleic acid samples with said forward and reverse primer pair wherein at least two of said multiple samples are characterised by the presence of a single copy of the nucleic acid region of interest;
(ii) amplifying the DNA samples of step (i) in accordance with a standardised quantitative PCR protocol, which protocol has been standardised to effect the amplification of a single copy of a reference DNA template molecule using a reference forward and reverse primer pair directed to said template molecule; and
(iii) determining the mean Ct of the amplification reactions of step (ii) and assessing the amplification efficiency of said primers from said Ct value.

In a further embodiment, the mean Ct value of the test primers and/or the reference primers has been determined by:
a) performing a limiting dilution of a biological sample comprising said DNA region of interest and generating multiple aliquots of said sample wherein a subgroup of said aliquots contain no copies of said DNA region of interest;
b) contacting the aliquots of step (a) with said forward and reverse primer pair and amplifying the DNA of step (a) in accordance with said standardised quantitative PCR protocol and determining the Ct of each aliquot;
c) statistically determining the proportion of aliquots from step (a) comprising at least two starting copies of said DNA region of interest; and
d) determining the mean Ct of the amplification reaction step (b) wherein the calculation of said mean excludes the Ct results obtained both from aliquots in which no amplification was observed and the proportion of lowest individual aliquot Ct results corresponding to the proportion value determined in step (b).

In one embodiment, said nucleic acid region of interest comprises a SNP, point mutation, hypermutation, chromosomal translocation, genomic gene segment rearrangement, DNA insertion, DNA deletion or breakpoint, such as a chromosomal breakpoint, a specific gene segment, a specific region, part or section of a gene or an intergenic region.

In another embodiment, said nucleic acid region of interest is the rearranged immunoglobulin (Ig) or T cell receptor (TCR) DNA, more particularly the rearranged V, D and/or J segments.

In yet another embodiment and in the context of V(D)J rearrangement, said nucleic acid region of interest corresponds to the DJ or VDJ rearrangements of IgH, TCR β or TCR δ. In another embodiment said nucleic acid region of interest corresponds to the VJ rearrangement of Igκ, Igλ, TCRα or TCRγ.

In still yet another embodiment, said nucleic acid region of interest is a V gene segment region, such as a region predisposed to undergoing hypermutation and/or a J gene segment region encoding a portion of the CDR3.

In yet still another embodiment, said nucleic acid region of interest is directed to gene segment regions encoding all or some of the V leader sequence, IgH FR1, IgH FR2 or IgH FR3.

In a further embodiment, said amplification reaction is PCR.

In another further embodiment the amplicons produced by said quantitative PCR are detected using a non-specific fluorescent dyes that intercalate with double-stranded DNA. In another embodiment the amplicons produced by said quantitative PCR are detected using a sequence-specific DNA probe operably linked to a reporter molecule such as a fluorescent reporter.

In still another further embodiment, said reference nucleic acid template is a rearranged IgH gene or TCR gene.

In yet another further embodiment, said reference nucleic acid template is a single copy gene, preferably the GALT gene.

As detailed hereinbefore, the mean Ct which is obtained from a standardised PCR assay amplifying one starting copy of a DNA region of interest provides an unexpectedly accurate and reproducible parameter by which to assess the amplification efficiency of a primer pair of interest. This assessment may be either relative or absolute. In order to enable this assessment, one must determine either one or both of the efficiency of the reference primers in amplifying the reference DNA template molecule using the standardised assay (herein referred as the "standardised reference assay") and/or the Ct from the amplification of single copy of the reference DNA template with the reference primer. Amplification efficiency determination of the standardised reference assay can be achieved by performing traditional Ct line regression modelling as hereinbefore described. However, other than this initial line regression analysis, which is performed in the context of an optimised and standardised assay, no further such modelling is required in terms of the primers which are subsequently tested using the standardised assay. Rather, the mean Ct value from the amplification of the test primers is the only value required to enable assessment of the amplification efficiency of the test primers in issue. In this regard, reference to "assessing" the amplification efficiency of a test primer should be understood as a reference to drawing a conclusion in relation to the efficiency of the subject test primer, whether that be a relative, absolute, qualitative or quantitative aspect of test primer efficiency. Such assessments include, but are not limited to:

(i) Drawing an inference on the amplification efficiency of a test primer from the mean Ct value, per se, wherein the lower the Ct value the better the primer efficiency. Since it is empirically known that at an amplification efficiency of 100% the Ct for one target copy will be 36.53 and for 95% efficiency will be 37.91, then where the standardised reference assay protocol was optimised to function at a high level of efficiency, test primer Ct values of less than 38 are indicative of good primer efficiency. In accordance with this form of analysis, the Ct value provides a measure of amplification efficiency but not the actual amplification efficiency;

(ii) Where the Ct of the amplification of a single copy of the reference template with the reference primer is, or has previously been, determined, the inference described in (i) can be performed via a comparison of the single target molecule Ct of the test primer relative to that of the reference primer. If the Ct resulting from amplification of a single copy of a test primer template under standardised conditions is of the order of that previously observed from amplification of a single copy of the reference template then it is possible to conclude that the test primer is operating at an efficiency of a similar order as the reference primer. Further, an increase in the Ct value of the test primer relative to the Ct of the reference primer would infer that the test primer exhibits poorer efficiency than the reference primer.

(iii) Where the slope of the line in a Ct line regression model of the standardised reference assay has been determined, the efficiency of that reaction can be determined using the formula:

$$E = 10^{-1/slope} - 1 \quad (4)$$

The relationship between the initial number of target molecules (No), amplification efficiency (E), cycle threshold (Ct) and the number of amplicons at threshold ($N_t$) is:

$$N_t = N_0 \cdot (1+E)^{Ct}$$

For the amplification of one target nucleic acid molecule, this formula simplifies to:

$$N_t = 1 \cdot (E+1)^{Ct} \quad (5)$$

Accordingly, $N_t$ can be calculated by determining the amplification efficiency of a reference primer under the standardised conditions described herein and by determining the Ct obtained by amplifying a single reference template molecule under those standardised conditions. Since $N_t$ is a constant and it has been surprisingly determined by the present inventors both that the Ct of a test primer amplifying a single copy of a target DNA molecule in said standardised assay is highly accurate and reproducible and that a reference primer and template molecule amplified under the same standardised conditions provide a reliable efficiency point of reference against which to analyse the test primer results, the efficiency of a test primer can be reliably and quickly determined using the formula (5) where the Ct is determined from the test primer amplification of a single copy of a target DNA and $N_t$ is calculated from the standardised reference assay. In a derivation of formula (5), the amplification efficiency of a test primer (Et) can be determined using formula (6):

$$E_{(test)} = N_{t(ref)}^{1/Ct(test)} - 1 \quad (6)$$

where the value of $N_t$ is determined from the reference primer amplification results, together with the number of cycles taken for the test primer amplification to reach threshold (Ct.t) when a single molecule of the test nucleic acid region of interest is amplified.

As detailed hereinbefore, the method of the present invention is rendered even more useful by virtue of the unexpected determination that even where the reference nucleic acid template selected for use exhibit little or no homology to the test primers and target nucleic acid of interest, its amplification in the standardised assay will produce comparable results to a standardised assay which is performed using reference primers and template which exhibit a higher level of homology to the test primers and target of interest, thereby unexpectedly enabling the application of a given standardised assay to a substantially broader scope of primers requiring efficiency assessment than just those primers which exhibit homology to the selected reference primers and template; and (iv) Where the amplification efficiency and Ct for amplifying one copy of the reference template with the reference primer are known, the efficiency of any test primer which is tested in the standardised assay can be quickly and easily calculated using only the efficiency and Ct values since $N_t$ is the same for both reference and test. More specifically, since Nt is a constant, then $E_r$ and $E_t$ (the amplification efficiencies of reference and test primers, respectively) and Ct.r and Ct.t (the cycles to threshold when single copy reference and test templates, respectively, are amplified) are related as follows:

$$1 \cdot (E_{(test)}+1)^{Ct(test)} = 1 \cdot (E_{(ref)}+1)^{Ct(ref)}$$

and therefore:

$$E_{(test)} = (E_{(ref)}+1)^{Ct(ref)/Ct(test)} - 1 \quad (7)$$

In one embodiment, said amplification efficiency is assessed relative to the efficiency point of reference determined from the amplification of the reference template DNA by the reference primers in the standardised assay.

In another embodiment, said efficiency point of reference is the mean Ct value of the reference primers and said amplification efficiency assessment is made by comparing the mean Ct value of the forward and reverse test primer pair directed to the DNA region of interest to the mean Ct value determined for the amplification of the reference forward and reverse primer pair directed to the reference DNA template molecule.

In yet another embodiment, said efficiency point of reference is $Nt_{(ref)}$ and said amplification efficiency assessment is made by using the mean Ct value of the forward and reverse primer pair directed the DNA region of interest ($Ct_{(test)}$) in the formula:

$$E_{(test)} = N_{t(ref)}^{1/Ct(test)} - 1$$

In still yet another embodiment, said efficiency point of reference is $E_{(ref)}$ and $C_{t(ref)}$ and said amplification efficiency assessment is made by using the mean Ct value of the forward and reverse primer pair directed the DNA region of interest ($Ct_{(test)}$) in the formula:

$$E_{(test)} = (E_{(ref)}+1)^{Ct(ref)/Ct(test)} - 1$$

In another embodiment, said nucleic acid region of interest comprises a SNP, point mutation, hypermutation, chromosomal translocation, genomic gene segment rearrangement, DNA insertion, DNA deletion or breakpoint, such as a chromosomal breakpoint, a specific gene segment, a specific region, part or section of a gene or an intergenic region.

In still another embodiment, said nucleic acid region of interest is the rearranged immunoglobulin (Ig) or T cell receptor (TCR) DNA, more particularly the rearranged V, D and/or J segments.

In yet another embodiment and in the context of V(D)J rearrangement, said nucleic acid region of interest corresponds to the DJ or VDJ rearrangements of IgH, TCR β or TCR δ. In another embodiment said nucleic acid region of interest corresponds to the VJ rearrangement of Igκ, Igλ, TCRα or TCRγ.

In still yet another embodiment, said nucleic acid region of interest is a V gene segment region, such as a region predisposed to undergoing hypermutation and/or a J gene segment region encoding a portion of the CDR3.

In yet still another embodiment, said nucleic acid region of interest is directed to gene segment regions encoding all or some of the V leader sequence, IgH FR1, IgH FR2 or IgH FR3.

In a further embodiment, said amplification reaction is PCR.

In another further embodiment the amplicons produced by said quantitative PCR are detected using a non-specific fluorescent dye that intercalates with double-stranded DNA. In another embodiment the amplicons produced by said quantitative PCR are detected using a sequence-specific DNA probe operably linked to a reporter molecule such as a fluorescent reporter.

In still another further embodiment, said reference nucleic acid template is a rearranged IgH gene or TCR gene.

In yet another further embodiment, said reference nucleic acid template is a single copy gene, preferably the GALT gene.

The method of the invention provides a means of assessing the efficiency of either or both of the forward and reverse primers of a primer pair which is designed for use in a quantitative amplification reaction, in particular a quantitative PCR. This method obviates the need to perform the traditional and time consuming line regression modelling to assess each primer of interest and now provides a quick, simple and more reliable means of assessing efficiency. Still further, by virtue of the design and application of a standardised system within which to test these primers, the efficacy of any primer tested within that system can be directly compared to any other primer which is tested in that system. Accordingly, where multiple primers have been designed to amplify a single target, the most efficient primer can be quickly and easily identified. In another example, where one may seek to transfer the performance of a standardised amplification protocol to new instrumentation (such as might occur in a new laboratory), or to otherwise alter some aspect of the reaction conditions, the assessment analyses options described above facilitate an accurate and simple recalibration of the assay. For example, a particularly simple approach for a new instrument would be to determine the number of amplicons at threshold by amplifying the reference nucleic acid template under the new conditions, determining the Ct of a single target template and thereby calculating the Nt. Test primer efficiencies could then be determined relative to these results. Since it has also been unexpectedly determined that an assay optimised and standardised using reference primers and template which exhibit little or no homology with the nucleic acid region of interest (such as the GALT gene) can be used, the scope of primers which can be tested within the context of a single standardised assay is broad, thereby further reducing the complexity and cost of testing a wide range of primers.

The present method can therefore be used to test and select for primers for use in diagnosis, prognosis, classification, prediction of disease risk, detection of recurrence of disease, immune surveillance or monitoring of prophylactic or therapeutic efficacy in the context or any disease or non-disease state which can be characterised by the expression of one or more target nucleotide sequences. Still further, this method has application in any other context where the analysis of sequences in certain target DNA and RNA regions or screening for the presence of specific target DNA and RNA sequences is necessitated, such as in the context of research and development or quality control for PCR. For example, the present invention provides a solution to current and emerging needs that scientists and the biotechnology industry are seeking to address in the fields of genomics, pharmacogenomics, drug discovery, food characterization and genotyping.

Using lymphoid neoplasia as a non-limited example, the present invention provides means for testing and selecting primers to use in qPCR reactions for determining whether a mammal (e.g. a human) has neoplasia, whether a biological sample taken from a mammal contains neoplastic cells or DNA derived from neoplastic cells, estimating the risk or likelihood of a mammal developing a neoplasm, monitoring the efficacy of anti-cancer treatment or selecting the appropriate treatment in a mammal with cancer. Such methods are based on the determination that lymphoid neoplasias are characterised by the clonal expansion of a cell expressing a unique V(D)J rearrangement.

The method of the invention enables the design of efficient primers which can be used to evaluate individuals known or suspected to have neoplasia, or as a routine clinical test in an individual not necessarily suspected to have a neoplasia. Further, the present methods may be used to assess the efficacy of a course of treatment. For example, the efficacy of an anti-cancer treatment can be assessed by monitoring MRD over time in a mammal having a lymphoid cancer. Typically, a reduction or absence of a clonal population characterised by a specific target nucleotide sequence in a biological sample taken from a mammal following treatment indicates efficacious treatment.

The method of the present invention is particularly useful in the context of applications such as the design of patient specific (e.g. MRD analysis) or disease specific primers where new primers are required to be constantly generated to detect and amplify a new or constantly mutating DNA target or where the DNA target differs for different patients. Where current methods for testing the efficacy of such primers will produce variable results or where accurate testing of different primers would consume inordinate resources, the method of the present invention provides a standardised system which enables primer efficiency to be objectively, consistently and quickly assessed and, if necessary, compared to the efficiency of any other primers tested in the same system. Accordingly, assuming that the standardised reference assay functions at a level of efficiency which is deemed appropriate by regulatory authorities or the like, the present method enables reference laboratories or in house laboratories to establish the standardised assay and thereafter test and certify the efficacy of primers of interest relative to a known and approved standard. It is contemplated that the reference primer and template molecules, for example, could be provided to a laboratory together with the details of the standardised protocol such that the assay could be established and validated any that laboratory. Alternatively, primers to be tested could be sent to a central reference laboratory for assessment.

Accordingly, in yet another aspect the present method is directed to a kit for facilitating assessment of the efficiency of a forward and reverse primer pair which are directed to a nucleic acid region of interest, said kit comprising a reference forward and reverse primer and instructions detailing the standardised amplification protocol method and/or minimum efficiency outcomes as herein before defined, optionally together with the reference nucleic acid template molecule as hereinbefore defined and reagent suitable for use in facilitating the amplification of the reference primers in accordance with the standardised protocol.

Further features of the present invention are more fully described in the following non-limiting examples.

Example 1

Development of a Standardised Protocol for One Copy Ct

Those skilled in the art will be familiar with the general principles of amplification exemplified in the subject protocol.

Reagents and Materials
   10×PCR R×n buffer (—MgCl$^2$) Life technologies for Platinum Taq 0966083
   MgCl$^2$ 50 mM Life technologies for Platinum Taq
   dNTP 10 mM mix Fisher Biotec DN-10M-10
   Primers Forward and reverse at 50 µM each IDT
   IghJ probe IDT custom LNA probe
   Platinum Taq Life technologies
   Tubes Eppendorf safe lock 1.5 ml
   Plate Bio-Rad Hard shell Low profile skirted 96-well PCR plates HSP-9601
   Instrument Bio-Rad CFX Connect.
Reaction Constituents/Well

TABLE 1

|  | µl |
| --- | --- |
| water | 16.45 |
| Buffer 10X | 2.5 |
| MgCl$_2$ 50 mM | 2.5 |
| dNTP 10 mM | 0.75 |
| Forward primer 50 µM | 0.2 |
| Forward primer 50 µM | 0.2 |
| Syto 82 50 µM | 0.25 |
| Probe IGHJ FAM µM | 0.2 |
| Platinum Taq 5 U/µl | 0.2 |
| DNA eg 2.5 pg | 2 |
| Final volume | 25 |

Temperature Protocol for the PCR
   91° c. 3 mins
   97° C., 15 sec; 72° C., 30 sec×5 cycles
   96° C., 15 sec; 72° C., 30 sec×5 cycles,
   94° C., 15 sec; 72° C., 30 sec×35 cycles
Notes
   For one-copy experiments the aim is to have a mean of approximately 0.5-1 copy of the target template in each well, as this will result in approximately 39%-63% of the wells being positive. For DNA from non-neoplastic cell populations, this can usually be achieved by aliquoting 2-4 pg DNA/well. When neoplastic cell populations are being studied, the neoplastic cells may comprise an unknown proportion of the total population and, if so, an initial study may can be performed to determine the approximate mass of DNA required for some wells to be positive and some wells to be negative.
   Syto82 was only used in some experiments and if not used was replaced by an equal volume of water. The concentration used had previously been shown not to inhibit the Ct. Syto82 monitors the accumulation of double-stranded DNA as the PCR progresses. It is a general probe, not a gene-specific probe. It gave the same results as gene-specific probes but occasional positive wells were negative with the gene-specific probe and its use was therefore omitted in later experiments.
   Several features of this standardised protocol differ slightly from the features of most PCR protocols. (a) the Taq concentration is relatively high (b) the denaturation temperatures during the PCR optimise denaturation of genomic DNA during the early cycles (c) the annealing temperature is higher than is used by most experimenters as the majority of primers being studied were long primers.
   The probe shown is that used for IGH PCRs. The relevant gene-specific probes were used for other genes. Setting of the threshold was done both by the operator and by the instrument algorithm. The instrument algorithm set the threshold higher than did the operator and the Ct provided by the instrument threshold was approximately 1.5 greater than that provided by the user threshold. Unless otherwise stated the results shown are those provided by the instrument.

Example 2

Determining the Number of Wells to Analyse

| positive wells | mean copies/ well | probabilities 0 | 1 | >1 | number of wells 0 | 1 | >1 | positive wells | number to select |
|---|---|---|---|---|---|---|---|---|---|
| 23 | 3.18 | 0.04 | 0.13 | 0.83 | 1 | 3 | 20 | 23 | 3 |
| 22 | 2.48 | 0.08 | 0.21 | 0.71 | 2 | 5 | 17 | 22 | 5 |
| 21 | 2.08 | 0.13 | 0.26 | 0.62 | 3 | 6 | 15 | 21 | 6 |
| 20 | 1.79 | 0.17 | 0.30 | 0.53 | 4 | 7 | 13 | 20 | 7 |
| 19 | 1.57 | 0.21 | 0.33 | 0.46 | 5 | 8 | 11 | 19 | 8 |
| 18 | 1.39 | 0.25 | 0.35 | 0.40 | 6 | 8 | 10 | 18 | 8 |
| 17 | 1.23 | 0.29 | 0.36 | 0.35 | 7 | 9 | 8 | 17 | 9 |
| 16 | 1.10 | 0.33 | 0.37 | 0.30 | 8 | 9 | 7 | 16 | 9 |
| 15 | 0.98 | 0.38 | 0.37 | 0.26 | 9 | 9 | 6 | 15 | 9 |
| 14 | 0.88 | 0.42 | 0.36 | 0.22 | 10 | 9 | 5 | 14 | 9 |
| 13 | 0.78 | 0.46 | 0.36 | 0.18 | 11 | 9 | 4 | 13 | 9 |
| 12 | 0.69 | 0.50 | 0.35 | 0.15 | 12 | 8 | 4 | 12 | 8 |
| 11 | 0.61 | 0.54 | 0.33 | 0.13 | 13 | 8 | 3 | 11 | 8 |
| 10 | 0.54 | 0.58 | 0.31 | 0.10 | 14 | 8 | 2 | 10 | 8 |
| 9 | 0.47 | 0.63 | 0.29 | 0.08 | 15 | 7 | 2 | 9 | 7 |
| 8 | 0.41 | 0.67 | 0.27 | 0.06 | 16 | 6 | 2 | 8 | 6 |
| 7 | 0.34 | 0.71 | 0.24 | 0.05 | 17 | 6 | 1 | 7 | 6 |
| 6 | 0.29 | 0.75 | 0.22 | 0.03 | 18 | 5 | 1 | 6 | 5 |
| 5 | 0.23 | 0.79 | 0.18 | 0.02 | 19 | 4 | 1 | 5 | 4 |
| 4 | 0.18 | 0.83 | 0.15 | 0.01 | 20 | 4 | 0 | 4 | 4 |
| 3 | 0.13 | 0.88 | 0.12 | 0.01 | 21 | 3 | 0 | 3 | 3 |
| 2 | 0.09 | 0.92 | 0.08 | 0.00 | 22 | 2 | 0 | 2 | 2 |

This example shows the method of selecting the particular wells to use for calculating the mean Ct and analyses 24 wells. The probability that a well originates from 0, 1 or more than 1 template is calculated using the observed number of positive wells and from the probabilities provided by the Poisson distribution. For example, if 13 wells are positive, probably nine will have originated from 1 template and 4 will have originated from 2 or more templates. Amplification originating from 2 or more templates will result in a lower Ct than amplification originating from 1 template. The 4 lowest Ct values are therefore discarded and the mean Ct is calculated from the remaining 9 Ct values.

Example 3

Calculation of Mean Ct from One Template Copy

| Ct | Ct arranged | count mean SD | minus outliers | count mean SD | accepted Ct's | accept or reject | final mean | SD | count |
|---|---|---|---|---|---|---|---|---|---|
| 28.85 | 29.83 | 19 | 29.83 | 19 | 29.83 | accept | 29.05 | 0.37 | 8 |
| N/A | 29.36 | 28.40 | 29.36 | 28.40 | 29.36 | | | | |
| 28.21 | 29.02 | 0.72 | 29.02 | 0.72 | 29.02 | | | | |
| 28.88 | 28.88 | | 28.88 | | 28.88 | | | | |
| 27.03 | 28.86 | | 28.86 | | 28.86 | number to | | | |
| 28.86 | 28.85 | | 28.85 | | 28.85 | accept | | | |
| N/A | 28.8 | | 28.8 | 8 | 28.8 | | | | |
| 27.84 | 28.78 | | 28.78 | | 28.78 | | | | |
| 29.83 | 28.77 | | 28.77 | | | | | | |
| 27.85 | 28.66 | | 28.66 | | | | | | |
| N/A | 28.37 | | 28.37 | | | | | | |
| 27.46 | 28.21 | | 28.21 | | | | | | |
| 27.83 | 27.85 | | 27.85 | | | | | | |
| 29.02 | 27.84 | | 27.84 | | | | | | |
| 27.53 | 27.83 | | 27.83 | | | | | | |
| 28.8 | 27.74 | | 27.74 | | | | | | |
| 28.77 | 27.53 | | 27.53 | | | | | | |
| N/A | 27.46 | | 27.46 | | | | | | |
| 28.37 | 27.03 | | 27.03 | | | | | | |
| 29.36 | | | | | | | | | |
| 28.78 | | | | | | | | | |
| 28.66 | | | | | | | | | |
| 27.74 | | | | | | | | | |
| N/A | | | | | | | | | |

Twenty-four aliquots from one sample were amplified at a dilution which produced some positive and some negative wells. Successive columns show: the Ct results; Ct results arranged in descending magnitude; any outliers removed; results removed if judged on the basis of Poisson probabilities to have resulted from amplification of more than one copy; the final mean, standard deviation and number of wells. In this example there were 19 positive wells and, based on the Poisson probabilities, the 11 lowest Ct results were discarded and the mean Ct value was determined from the remaining 8.

Example 4

Results

|  | IGH reference 105-16 | | IGH population | | reference GALT gene | |
| --- | --- | --- | --- | --- | --- | --- |
|  | slopes | single copy Ct | slopes | single copy Ct | slopes | single copy Ct |
| mean | −3.352 | 38.89 | −3.39 | 38.80 | −3.27 | 39.07 |
| SD | 0.180 | 0.25 | 0.21 | 0.24 | 0.21 | 0.75 |
| n | 10 | 12 | 20 | 39 | 18 | 19 |
| CV | 5.4% | 0.63% | 6.1% | 0.63% | 6.5% | 1.91% |
| amp efficiency | 98.8% | | 97.1% | | 102.1% | |
| targets at threshold | $4.02 \times 10^{11}$ | | $2.71 \times 10^{11}$ | | $8.79 \times 10^{11}$ | |

This Example provides a summary of slopes and single copy Ct results. For each of the 2 reference genes the results are based on multiple experiments each involving the same template sequence together with the corresponding primers to it. The results for the IGH population comprise IGH sequences from different patients together with the 2 primers directed to each sequence. The same probe was used for all IGH PCRs. The Ct results for the Table were those determined using the software algorithm provided for the instrument. The substantial difference in precision between slope estimations and single copy estimations should be noted.

The results for amplification efficiency are derived from the slope estimations only.

The results for targets at threshold are based on both the amplification efficiency and the mean single copy Ct.

Example 5

95% Confidence Intervals of Amplification Efficiency

| primers | volume | DNA | number of primers | amplification efficiency mean | 95% confidence interval |
| --- | --- | --- | --- | --- | --- |
| IGH | 25 µl | — | 29 | 98.8% | 96.4%-101.4% |
| IGH | 50 µl | 1 µg | 21 | 96.4% | 95.2%-97.7% |
| TCR | 25 µl | — | 8 | 99.4% | 98.0%-100.6% |
| MRD | 50 µl | 1 µg | 50 | 97.0% | 93.2%-102.3% |

This table shows the means and the 95% confidence intervals for the amplification efficiencies of various groups of primers. The Ct results had been determined from the threshold set by the operator rather than by the software algorithm. Threshold set by the operator results in a Ct approximately 1.5 units less than that set by the software algorithm. The IGH and TCR results refer to analytical studies of primers in the laboratory, the MRD results were a retrospective analysis of data obtained during MRD assays. Amplification efficiencies were calculated from the one copy Ct results and from the reference value of $1.1 \times 10^{11}$ for the number of amplicons at threshold. Since variation of a one copy Ct result could result either from random experimental error or by variation between primers, an analysis of the variance was performed for each group in order to determine the between-primer variance, and this value and the mean value were used to determine the 95% confidence interval of amplification efficiency.

Example 6

Results for a Variety of Genes

| gene | one copy Ct | slope | amplification efficiency | targets at threshold |
| --- | --- | --- | --- | --- |
| IGH population | 38.80 | −3.39 | 97.1% | $2.7 \times 10^{11}$ |
| IGH 105-16 reference | 38.89 | −3.35 | 98.8% | $4.0 \times 10^{11}$ |
| GALT reference | 39.07 | −3.27 | 102.1% | $8.8 \times 10^{11}$ |
| Nras | 38.52 | −3.35 | 98.8% | $3.2 \times 10^{11}$ |
| APC | 39.24 | −3.37 | 98.0% | $4.4 \times 10^{11}$ |
| T-rec | 39.25 | −3.30 | 100.8% | $7.7 \times 10^{11}$ |
| TCR population | 38.90 | −3.32 | 100.2% | $8.1 \times 10^{11}$ |
| AAAS | 39.2 | | | |
| CINP | 39.8 | | | |
| CALR | 37.9 | | | |
| DCTD | 38.5 | | | |

The results show the high degree of concordance which is seen when primers for different genes are analysed in order to determine amplification efficiency as derived from one copy Ct and slope. All the gene targets were amplified under the standardised conditions but a specific probe was used for each gene. The Ct results for the Table were those determined using the software algorithm provided for the instrument. The numbers for the IGH population and reference have been previously given. The GALT reference results were based on 22 estimations of the one copy Ct and slope and for the remaining genes the results given for each were based on at least 2 estimations for each of one copy Ct and slope. The TCR results are heterogeneous as they comprise estimations for both TCRβ and TCRγ genes and the results for TCRβ include results involving 3 different probes for different targets.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Bruggemann M, van der Velden V H, Raff T, Droese J, Ritgen M, Pott C, et al. Rearranged T-cell receptor beta genes represent powerful targets for quantification of minimal residual disease in childhood and adult T-cell acute lymphoblastic leukemia. Leukemia. 2004; 18(4): 709-19.

Nakao M, Janssen J W, Flohr T, Bartram C R. Rapid and reliable quantification of minimal residual disease in acute lymphoblastic leukemia using rearranged immunoglobulin and T-cell receptor loci by LightCycler technology. Cancer Res. 2000; 60(12):3281-9.

Pongers-Willemse M J, Seriu T, Stolz F, d'Aniello E, Gameiro P, Pisa P, et al. Primers and protocols for standardized detection of minimal residual disease in acute lymphoblastic leukemia using immunoglobulin and T cell receptor gene rearrangements and TAL1 deletions as PCR targets: report of the BIOMED-1 CONCERTED ACTION: investigation of minimal residual disease in acute leukemia. Leukemia. 1999; 13(1):110-8.

van der Velden V H, Boeckx N, van Wering E R, van Dongen J J. Detection of minimal residual disease in acute leukemia. J Biol Regul Homeost Agents. 2004; 18(2): 146-54.

van der Velden V H, Panzer-Grumayer E R, Cazzaniga G, Flohr T, Sutton R, Schrauder A, et al. Optimization of PCR-based minimal residual disease diagnostics for childhood acute lymphoblastic leukemia in a multi-center setting. Leukemia. 2007; 21(4):706-13.

van der Velden V H, van Dongen J J. MRD detection in acute lymphoblastic leukemia patients using Ig/TCR gene rearrangements as targets for real-time quantitative PCR. Methods Mol Biol. 2009; 538:115-50.

van der Velden V H, Wijkhuijs J M, Jacobs D C, van Wering E R, van Dongen J J. T cell receptor gamma gene rearrangements as targets for detection of minimal residual disease in acute lymphoblastic leukemia by real-time quantitative PCR analysis. Leukemia. 2002; 16(7): 1372-80.

van der Velden V H, Willemse M J, van der Schoot C E, Hahlen K, van Wering E R, van Dongen J J. Immunoglobulin kappa deleting element rearrangements in precursor-B acute lymphoblastic leukemia are stable targets for detection of minimal residual disease by real-time quantitative PCR. Leukemia. 2002; 16(5):928-36.

van der Velden V H J, Noordijk R, Brussee M, Hoogeveen P, Homburg C, de Haas V, C. van der Schoot E, van Dongen J J M. Minimal residual disease diagnostics in acute lymphoblastic leukaemia: Impact of primer characteristics and size of junctional regions. British Journal of Haematology, 2014, 164, 451-464

Verhagen O J, Willemse M J, Breunis W B, Wijkhuijs A J, Jacobs D C, Joosten S A, et al. Application of germline IGH probes in real-time quantitative PCR for the detection of minimal residual disease in acute lymphoblastic leukemia. Leukemia. 2000; 14(8):1426-35.

The invention claimed is:

1. A method of assessing the amplification efficiency of a forward and reverse primer pair directed to a nucleic acid region of interest, said method comprising:
   (i) contacting a nucleic acid sample with said forward and reverse primer pair wherein said nucleic acid sample is characterised by the presence of a single molecule of the nucleic acid region of interest;
   (ii) amplifying the nucleic acid sample of step (i) in accordance with a standardised quantitative amplification protocol, which protocol has been standardised to effect the amplification of a single molecule of a reference nucleic acid template molecule using a reference forward and reverse primer pair directed to said template molecule; and
   (iii) determining the Ct of the amplification reaction of step (ii) and assessing the amplification efficiency of said primers from said Ct value.

2. The method according to claim 1 wherein said nucleic acid is DNA.

3. The method according to claim 1 wherein said nucleic acid region of interest is a SNP, point mutation, hypermutation, chromosomal translocation, genomic gene segment rearrangement, DNA insertion, DNA deletion or breakpoint, a specific gene segment, a specific region, part or section of a gene or an intergenic region.

4. The method according to claim 1 wherein said nucleic acid region of interest is the rearranged immunoglobulin (Ig) or T cell receptor (TCR) DNA.

5. The method according to claim 4 wherein said rearranged immunoglobulin (Ig) or T cell receptor (TCR) DNA is the rearranged V, D and/or J segments.

6. The method according to claim 5 wherein said rearranged V, D and/or J segments are the DJ or VDJ rearrangement of IgH, TCR β or TCR δ.

7. The method according to claim 5 wherein said rearranged V, D and/or J segment is the VJ rearrangement of Igκ, Igλ, TCRα or TCRγ.

8. The method according to claim 1 wherein said nucleic acid region of interest is a V gene segment region and/or a J gene segment region.

9. The method according to claim 8 wherein said V gene segment region is a region predisposed to undergoing hypermutation and said J gene segment region encodes a portion of the CDR3.

10. The method according to claim 1 wherein said nucleic acid region of interest is directed to gene segment regions encoding all or some of the V leader sequence, IgH FR1, IgH FR2 or IgH FR3.

11. The method according to claim 1 wherein said amplification is the polymerase chain reaction.

12. The method according to claim 11 wherein said amplicons produced by said quantitative PCR are detected using a non-specific intercalating fluorescent dye.

13. The method according to claim 11 wherein said amplicons produced by said quantitative PCR are detected using a sequence-specific DNA probe operably linked to a reporter molecule.

14. The method according to claim 13 wherein said reporter molecule is a fluorescent dye.

15. The method according to claim 12 wherein said fluorescent dye is fluorescein.

16. The method according to claim 1 wherein said reference nucleic acid template is a rearranged IgH gene or TCR gene or single copy gene, preferably the GALT gene.

17. The method according to claim 16 wherein said forward and reverse primers directed to a nucleic acid region of interest are configured to amplify rearranged Ig or TCR DNA.

18. A method of determining the Ct of a forward and reverse primer pair directed to a nucleic acid region of interest, said method comprising:
   (i) contacting multiple aliquots of a nucleic acid samples with said forward and reverse primer pair wherein at least two of said multiple aliquots are characterised by the presence of a single molecule of the nucleic acid region of interest;
   (ii) amplifying the nucleic acid aliquots of step (i) in accordance with a quantitative amplification protocol designed to effect the amplification of a single molecule of a nucleic acid target molecule and determining the Ct of each aliquot; and
   (iii) determining the mean Ct of the amplification reactions of step (ii) which amplified from said single molecule of the nucleic acid region of interest.

19. The method according to claim 18 wherein said method comprises:
   (i) performing a limiting dilution of a biological sample comprising said DNA region of interest and generating multiple aliquots of said sample wherein a subgroup of said aliquots contain no molecules of said DNA region of interest;
   (ii) contacting the aliquots of step (i) with said forward and reverse primer pair and amplifying said aliquots in accordance with a quantitative amplification protocol designed to effect the amplification of a single molecule of said DNA region of interest and determining the Ct of each aliquot;
   (iii) statistically determining the proportion of aliquots from step (i) comprising at least two starting molecules of said DNA region of interest; and
   (iv) determining the mean Ct of the amplification reactions of step (ii) wherein the calculation of said mean excludes the Ct results obtained both from aliquots in which no amplification was observed and the proportion of lowest individual aliquot Ct results corresponding to the proportion value determined in step (iii).

20. The method according to claim 1 wherein said method comprises:
   (i) contacting multiple aliquots of a nucleic acid sample with said forward and reverse primer pair wherein at least two of said multiple aliquots are characterised by the presence of a single molecule of the nucleic acid region of interest;
   (ii) amplifying the DNA aliquots of step (i) in accordance with a standardised quantitative PCR protocol, which protocol has been standardised to effect the amplification of a single molecule of a reference DNA template molecule using a reference forward and reverse primer pair directed to said template molecule; and
   (iii) determining the mean Ct of the amplification reactions of step (ii) and assessing the amplification efficiency of said primers from said Ct value.

21. The method according to claim 20 wherein the mean Ct value of the test primers and/or the reference primers has been determined in accordance with a method comprising:
   (i) contacting multiple aliquots of a nucleic acid samples with said forward and reverse primer pair wherein at least two of said multiple aliquots are characterised by the presence of a single molecule of the nucleic acid region of interest;
   (ii) amplifying the nucleic acid aliquots of step (i) in accordance with a quantitative amplification protocol designed to effect the amplification of a single molecule of a nucleic acid target molecule and determining the Ct of each aliquot; and
   (iii) determining the mean Ct of the amplification reactions of step (ii) which amplified from said single molecule of the nucleic acid region of interest.

22. The method according to claim 1 wherein said amplification efficiency is assessed relative to the efficiency point of reference determined from the amplification of the reference template DNA by the reference primers in the standardised assay.

23. The method according to claim 22 wherein said efficiency point of reference is the mean Ct value of the reference primers and said amplification efficiency assessment is made by comparing the mean Ct value of the forward and reverse primer pair directed the DNA region of interest to the mean Ct value determined for the amplification of the reference forward and reverse primer pair directed to the reference DNA template molecule.

24. The method according to claim 22 wherein said efficiency point of reference is $Nt_{(ref)}$ and said amplification efficiency assessment is made by using the mean Ct value of the forward and reverse primer pair directed the DNA region of interest ($Ct_{(test)}$) in the formula:

$$E_{(test)} = N_{t(ref)}^{1/Ct(test)} - 1.$$

25. The method according to claim 22 wherein said efficiency point of reference is $E_{(ref)}$ and $C_{t(ref)}$ and said amplification efficiency assessment is made by using the mean Ct value of the forward and reverse primer pair directed the DNA region of interest ($Ct_{(test)}$) in the formula:

$$E_{(test)} = (E_{(ref)} + 1)^{Ct(ref)/Ct(test)} - 1.$$

26. A kit for facilitating assessment of the efficiency of a forward and reverse primer pair which are directed to a nucleic acid region of interest, said kit comprising a reference forward and reverse primer and instructions detailing the standardised amplification protocol method and/or minimum efficiency outcomes as defined in claim 1, optionally together with the reference nucleic acid template molecule as defined in claim 1 and reagent suitable for use in facilitating the amplification of the reference primers in accordance with the standardised protocol.

* * * * *

SEQUENCE LISTING

<160> NUMBER OF SEQ ID NOS: 3

<210> SEQ ID NO 1
<211> LENGTH: 955
<212> TYPE: DNA
<213> ORGANISM: Artificial Sequence
<220> FEATURE:
<223> OTHER INFORMATION: target sequence for amplification
<220> FEATURE:
<221> NAME/KEY: misc_feature
<222> LOCATION: 3, 4, 5, 6, 7, 8, 9, 10, 11, 12, 13, 16, 18, 19, 20,
    513, 630, 631, 632, 636, 697, 806, 824, 831, 839, 851, 856, 860,
    869, 871, 878, 903, 905, 906, 908, 914, 915, 922, 937, 939, 946,
    950, 953, 954
<223> OTHER INFORMATION: n = A,T,C or G

<400> SEQUENCE: 1

```
ggnnnnnnnn nnnggncnnn ccgcgggaat tcgattcgac caccacccca cagtattacg      60
atattttggg gccctactac tacggtatgg acgtctgggg ccaagggacc acggtcaccg     120
tctcctcagg taagaatggc cactctaggg cctttgtttt ctgctactgc ctgtggggtt     180
tcctgagcat tgcaggttgg tcctcggggc atgttccgag gggacctggg caatcactag     240
tgaattcgcg gccgcctgca ggtcgaccat atgggagagc tcccaacgcg ttggatgcat     300
agcttgagta ttctatagtg tcacctaaat agcttggcgt aatcatggtc atagctgttt     360
cctgtgtgaa attgttatcc gctcacaatt ccacacaaca tacgagccgg aagcataaag     420
```

```
tgtaaagcct gggtgccta atgagtgagc taactcacat taattgcgtt gcgctcactg    480
cccgctttcc agtcgggaaa cctgtcgtgc canctgcatt aatgaatcgg ccaacgcgcg    540
gggagaggcg gtttgcgtat tgggcgctct tccgcttcct cgctcactga ctcgctgcgc    600
tcggtcgttc ggctgcggcg agcggtatcn nntcantcaa aggcggtaat acggttatcc    660
acagaatcag gggataacgc aggaaagaac atgtgancaa aaggccagca aaaaggccag    720
gaaccgtaaa aaggccgcgt tgctggcgtt tttccatagg gctccgcccc cctgacgagc    780
atcacaaaaa tcgacgctca agtcanaggt ggcgaaaccc gacnggacta naaagatana    840
ggcgtttccc ncctgnaaan tccctcgng ngctctcntg ttccgaccct gccgctttac    900
cgnanncntg ttcnnctttc tnccttcgg gaagcgngnc gctttnctcn tannt          955

<210> SEQ ID NO 2
<211> LENGTH: 27
<212> TYPE: DNA
<213> ORGANISM: Artificial Sequence
<220> FEATURE:
<223> OTHER INFORMATION: primer for amplification

<400> SEQUENCE: 2
cgaccaccac cccacagtat tacgata                                         27

<210> SEQ ID NO 3
<211> LENGTH: 21
<212> TYPE: DNA
<213> ORGANISM: Artificial Sequence
<220> FEATURE:
<223> OTHER INFORMATION: primer for amplification

<400> SEQUENCE: 3
atgttccgag gggacctggg c                                               21
```